United States Patent
Ackermann et al.

(10) Patent No.: US 8,377,953 B2
(45) Date of Patent: Feb. 19, 2013

(54) ISOTHIAZOLE AND PYRAZOLE DERIVATIVES AS FUNGICIDES

(75) Inventors: Peter Ackermann, Pfeffingen (CH); Carla Bobbio, Stein (CH); Camilla Corsi, Stein (CH); Ann Monica McGinley, Riehen (CH); Andreas Verras, New York, NY (US); Ruud Titulaeu, Nijmegen (NL); Josef Ehrenfreund, Allschwil (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 7 days.

(21) Appl. No.: 12/668,435

(22) PCT Filed: Jul. 9, 2008

(86) PCT No.: PCT/EP2008/005589
§ 371 (c)(1),
(2), (4) Date: Jan. 21, 2011

(87) PCT Pub. No.: WO2009/007098
PCT Pub. Date: Jan. 15, 2009

(65) Prior Publication Data
US 2011/0224241 A1 Sep. 15, 2011

(30) Foreign Application Priority Data
Jul. 11, 2007 (GB) .................................. 0713479.4

(51) Int. Cl.
*A61K 31/506* (2006.01)
*A61K 31/4439* (2006.01)
*A01N 43/56* (2006.01)
*A01N 43/80* (2006.01)
*A01P 3/00* (2006.01)
*A61P 31/10* (2006.01)
*C07D 401/06* (2006.01)
*C07D 417/06* (2006.01)

(52) U.S. Cl. ................................... 514/269

(58) Field of Classification Search .................. None
See application file for complete search history.

(56) References Cited

U.S. PATENT DOCUMENTS

2003/0018197 A1* 1/2003 Dymock et al. ........... 546/275.4
2011/0301034 A1* 12/2011 Corsi et al. ................. 504/253

FOREIGN PATENT DOCUMENTS

| DE | 10034129 | 6/2001 |
| WO | 0155142 | 8/2001 |
| WO | WO 2004065394 A1 * | 8/2004 |
| WO | 2006031631 | 3/2006 |

OTHER PUBLICATIONS

Gotthardt et al., Reactions of a thieno[3,4-c]isothiazole with 1,2,4-triazoline-3,5-diones and alkynes, 10 Liebigs Annalen Der Chemie 1796-803 (1986) (CAS Abstract).*
Alberola et al., 3,5-Dimethyl-4-isothiazolylmagnesium iodide and its reactions with some electrophilic reagents, 17(10) Synthetic Communications 1207-15 (1987) (CAS Abstract).*
Alberola et al., Synthesis of 4-acyl- and 4-alkenyl-3,5-dimethylisothiazole derivatives, 25(1) J. Heterocyclic Chem. 235-49 (1988) (CAS Abstract).*
Mukai et al., The fragmentation reaction of 4-(7-tropyl)pyrazoles by bromination, 37 (7) Bulletin Chem .Soc. Japan 1018-23 (1964) (CAS Abstract).*

* cited by examiner

*Primary Examiner* — Janet Andres
*Assistant Examiner* — Timothy R Rozof
(74) *Attorney, Agent, or Firm* — R. Kody Jones

(57) ABSTRACT

The present invention relates to compounds of Formula (I) wherein $R^1$, $R^2$, $R^3$ or $R^4$ are as defined in claim 1 or a salt or N-oxide thereof and their use in methods for the control and/or prevention of fungal infection, particularly in plants. The compounds claimed are isothiazole and pyrazole derivatives.

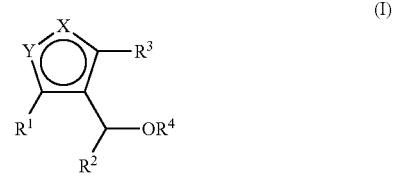

(I)

20 Claims, No Drawings

ISOTHIAZOLE AND PYRAZOLE DERIVATIVES AS FUNGICIDES

This application is a 371 of International Application No. PCT/EP2008/005589 filed Jul. 9, 2008, which claims priority to GB 0713479.4 filed Jul. 11, 2007, the contents of which are incorporated herein by reference.

The present invention relates to novel substituted isothiazoles and pyrazole-containing compounds, and their use in methods for the control and/or prevention of fungal infection, particularly in plants.

The incidence of serious fungal infections, either systemic or topical, continues to increase for plants, animals, and humans. Many fungi are common in the environment and not harmful to plants or mammals. However, some fungi can produce disease in plants, humans and/or animals.

Fungicides are compounds, of natural or synthetic origin, which act to protect plants against damage caused by fungi, including oomycetes. Current methods of agriculture rely heavily on the use of fungicides. In fact, some crops cannot be grown usefully without the use of fungicides. Using fungicides allows a grower to increase the yield of the crop and consequently, increase the value of the crop. Numerous fungicidal agents have been developed. However, the treatment of fungal infestations and infections continues to be a major problem. Furthermore, fungicide and antifungal drug resistance has become a serious problem, rendering these agents ineffective for some agricultural and therapeutic uses. As such, a need exists for the development of new fungicidal and antifungal compounds.

Accordingly, the present invention provides a compound of formula I:

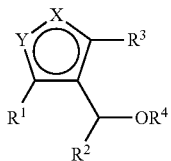

wherein:
X is S, N or $NR^5$ and Y is N or $NR^5$ with the proviso that one, but not both, of X or Y is N;
$R^1$ and $R^3$ are, independently, hydrogen, or optionally substituted alkyl, alkenyl, alkynyl, heterocyclyl, trialkylsilyl, arylalkyl, aryloxyalkyl, arylthioalkyl, aryl or heteroaryl, with the proviso that they are not both hydrogen;
$R^2$ is optionally substituted alkyl, alkenyl, alkynyl, heterocyclyl, arylalkyl, aryl or heteroaryl;
$R^4$ is hydrogen or a group which under biological conditions can be cleaved to form an alcohol at this position (i.e. —$OR^4$ is —OH). Examples of such groups are acyl, haloacyl, alkoxycarbonyl, aryloxycarbonyl, alkylaminocarbonyl or dialkylaminocarbonyl groups;
$R^5$ is hydrogen or optionally substituted alkyl, alkenyl, alkynyl, heterocyclyl, trialkylsilyl, arylalkyl, aryloxyalkyl, arylthioalkyl, aryl or heteroaryl;
or a salt or N-oxide thereof.

Unless otherwise stated, the following terms used in the specification and claims have the meanings given below:

"Alkyl" means a linear saturated monovalent hydrocarbon radical of one to eight carbon atoms or a branched saturated monovalent hydrocarbon radical of three to eight carbon atoms, e.g. methyl, ethyl, n-propyl, iso-propyl, n-butyl, sec-butyl, iso-butyl, tert-butyl, n-pentyl, iso-amyl, n-hexyl and the like. It is noted that this definition applies both when the term is used alone and when it is used as part of a compound term, such as "haloalkyl" and similar terms. Preferably, linear alkyl groups contain one to six carbon atoms, more preferably one to four carbon atoms and most preferably are selected from methyl, ethyl or n-propyl. Preferably, branched alkyl groups contain three to six carbon atoms and more preferably are selected from iso-propyl (1-methylethyl), sec-butyl (1-methylpropyl), iso-butyl (2-methylpropyl), tert-butyl (1,1-dimethylethyl) or iso-amyl (3-methylbutyl).

"Alkenyl" means a linear monovalent saturated hydrocarbon radical of two to eight carbon atoms, or a branched monovalent hydrocarbon radical of three to eight carbon atoms containing at least one double bond, e.g. ethenyl, propenyl and the like. Where appropriate, an alkenyl group can be of either the (E)- or (Z)-configuration. Preferably, linear alkenyl groups contain two to six carbon atoms and more preferably are selected from ethenyl, prop-1-enyl, prop-2-enyl, prop-1,2-dienyl, but-1-enyl, but-2-enyl, but-3-enyl, but-1,2-dienyl and but-1,3-dienyl. Preferably, branched alkenyl groups contain three to six carbon atoms and more preferably are selected from 1-methylethenyl, 1-methylprop-1-enyl, 1-methylprop-2-enyl, 2-methylprop-1-enyl and 2-methylprop-2-enyl.

"Alkyl" and "alkenyl" groups also encompass cycloalkyl and cycloalkenyl groups, respectively. These are monovalent cyclic hydrocarbon radicals of three to eight ring carbons and, more preferably, three to six ring carbons. Cycloalkyl groups are fully saturated, while cycloalkenyl groups may be mono- or di-unsaturated. Preferably, cycloalkyl groups are selected from cyclopropyl, cyclobutyl, cyclopentyl and cyclohexyl. Preferably, mono-unsaturated cycloalkenyl groups are selected from cyclobutenyl, cyclopentenyl and cyclohexenyl.

"Heterocyclyl" means a cyclic hydrocarbon radical as defined above containing one, two or three ring heteroatoms selected from N, O or $S(O)_n$ (where n is an integer from 0 to 2), the remaining ring atoms being carbon where one or two carbon atoms may optionally be replaced by a carbonyl group. Examples of such rings include, but are not limited to, oxirane, oxetane, tetrahydrofuran, tetrahydropyran, 1,3-dioxolane, 1,4-dioxane, aziridine, azetidine, pyrrolidine, piperidine, oxazinane, morpholine, thiomorpholine, imidazolidine, pyrazolidine and piperazine. More preferably, the heterocyclyl group contains three to six ring atoms including one O and/or one N ring atom.

"Alkynyl" means a linear monovalent saturated hydrocarbon radical of two to eight carbon atoms, or a branched monovalent hydrocarbon radical of five to eight carbon atoms, containing at least one triple bond, e.g. ethynyl, propynyl and the like. Preferably, linear alkynyl groups contain two to six carbon atoms and more preferably are selected from ethynyl, prop-1-ynyl, prop-2-ynyl, but-1-ynyl, but-2-ynyl and but-3-ynyl. Preferably, branched alkynyl groups contain four to six carbon atoms and more preferably are selected from 1-methylprop-2-ynyl, 3-methylbut-1-ynyl, 1-methylbut-2-ynyl, 1-methylbut-3-ynyl and 1-methylbut-3-ynyl.

"Alkoxy" means a radical —OR, where R is alkyl, alkenyl or alkynyl. Alkoxy groups include, but are not limited to, methoxy, ethoxy, 1-methylethoxy, propoxy, 1-methylpropoxy and 2-methylpropoxy. Preferably alkoxy means methoxy or ethoxy.

"Alkylthio" means a radical —SR, where R is alkyl, alkenyl or alkynyl. Alkylthio groups include, but are not limited to, methylthio, ethylthio, tert-butylthio, hexylthio, and the like.

"Aryl" or "aromatic ring moiety" refers to an aromatic substituent which may be a single ring or multiple rings which are fused together, linked covalently or linked to a common group such as an ethylene or methylene moiety. The aromatic rings may each contain one or more heteroatoms and hence "aryl" encompasses "heteroaryl". Representative examples of aryl include, for example, azulenyl, indanyl, indenyl, naphthyl, phenyl, tetrahydronaphthyl, biphenyl, diphenylmethyl, 2,2-diphenyl-1-ethyl, thienyl, pyridyl, pyrimidinyl and quinoxalyl. "Aryl" means substituted or unsubstituted aryl unless otherwise indicated and hence the aryl moieties may be optionally substituted with one or more of the same or different halogen atoms and/or one or more other groups such as nitro, carboxyl, alkoxy, phenoxy and the like. Additionally, the aryl radicals may be attached to other moieties at any position on the aryl radical which would otherwise be occupied by a hydrogen atom (such as, for example, 2-pyridyl, 3-pyridyl and 4-pyridyl).

In particular, "heteroaryl" means a cyclic, aromatic ring in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from O, N, and S. The heteroaryl group, including the ring carbons and each heteroatom, can be unsubstituted or substituted with from 1 to 4 substituents, as chemically feasible. For example, the heteroatom S may be substituted with one or two oxo groups, which may be shown as =O.

"Halo" or "halogen" means fluoro, chloro, bromo or iodo, preferably chloro or fluoro.

"Haloalkyl" means alkyl as defined above substituted with one or more of the same or different halo atoms. Examples of haloalkyl groups include, but are not limited to chloromethyl, fluoromethyl, difluoromethyl, trifluoromethyl, 2-fluoroethyl, 2-trifluoroethyl, 2-chloro-ethyl, 2-iodoethyl, 3-fluoropropyl, 3-chloropropyl, 2-trifluoro-1-chloroethyl and 1-difluoro-2-difluoro-3-trifluoropropyl.

"Haloalkenyl" means alkenyl as defined above substituted with one or more of the same or different halo atoms. Examples of haloalkenyl groups include, but are not limited to 2-dibromoethenyl, 2-fluoro-2-bromoethenyl, 5-bromopent-3-enyl and 3 dichloroprop-2-enyl.

"Haloalkynyl" means alkynyl as defined above substituted with one or more of the same or different halo atoms.

"Haloalkoxy" means a radical —OR, wherein R is haloalkyl or haloalkenyl.

"Haloalkylthio" means a radical —SR, wherein R is haloalkyl.

"Trialkylsilyl" means the group —Si(R)$_3$, wherein each R is, independently, an alkyl group as defined above.

"Arylalkyl" means a radical —R$^a$R$^b$ where R$^a$ is an alkylene or alkenylene group as defined below and R$^b$ is an aryl group as defined above. In particular, arylalkyl includes among others benzyl groups.

"Alkylene" means a linear saturated divalent hydrocarbon radical of one to six carbon atoms or a branched saturated divalent hydrocarbon radical of three to six carbon atoms, e.g. methylene, ethylene, propylene, 2-methylpropylene and the like. Preferred alkylene groups are the divalent radicals of the alkyl groups defined above.

"Alkenylene" means a linear divalent hydrocarbon radical of two to six carbon atoms or a branched divalent hydrocarbon radical of three to six carbon atoms, containing at least one double bond, e.g. ethenylene, propenylene and the like. Preferred alkenylene groups are the divalent radicals of the alkenyl groups defined above.

"Aryloxyalkyl" means a radical —R$^a$OR$^b$, wherein R$^a$ is an alkylene or alkenylene group and R$^b$ is an aryl group as defined above.

"Arylthioalkyl" means a radical —R$^a$SR$^b$, wherein R$^a$ is an alkylene or alkenylene group and R$^b$ is an aryl group as defined above.

"Acyl" means —C(O)R, wherein R is hydrogen, alkyl, alkenyl, alkynyl, heterocyclyl, aryl or heteroaryl. Examples of acyl groups include formyl, alkylcarbonyl, alkenylcarbonyl and arylcarbonyl groups.

"Haloacyl" means —C(O)R, wherein R is haloalkyl or haloalkenyl.

"Alkoxycarbonyl" means —C(O)OR, wherein R is hydrogen, alkyl, alkenyl, or alkynyl.

"Aryloxycarbonyl" means —C(O)OR, wherein R is aryl.

"Alkylaminocarbonyl" means —C(O)NHR, wherein R is alkyl.

"Dialkylaminocarbonyl" means —C(O)N(R)$_2$, wherein each R is independently alkyl.

"Cyano" means a —CN group.

"Hydroxy" or "hydroxyl" means an —OH group.

"Nitro" means an —NO$_2$ group.

"Oxy" means an —O— moiety.

"Thio" as used herein, refers to a —S— moiety.

"Optionally substituted" means substituted by one or more substituents, in particular, one, two, three or four substituents, independently selected from halogen, hydroxyl, cyano, nitro, alkyl, haloalkyl, alkenyl, haloalkenyl, alkynyl, haloalkynyl, heterocyclyl, aryl, heteroaryl, alkoxy, haloalkoxy, alkylthio, haloalkylthio, acyl, alkoxycarbonyl and trialkylsilyl. Preferred optional substituents include halogen (in particular, fluoro, chloro or bromo), cyano, nitro, alkyl (in particular, methyl and ethyl), haloalkyl, alkenyl, haloalkenyl, alkynyl, alkoxy (in particular, methoxy or ethoxy), haloalkoxy, alkylthio, haloalkylthio.

The compounds of formula I may exist in different geometric or optical isomeric forms or in different tautomeric forms. One or more centres of chirality may be present, in which case compounds of the formula I may be present as pure enantiomers, mixtures of enantiomers, pure diastereomers or mixtures of diastereomers. There may be double bonds present in the molecule, such as C=C or C=N bonds, in which case compounds of formula I may exist as single isomers of mixtures of isomers. Centres of tautomerisation may be present. This invention covers all such isomers and tautomers and mixtures thereof in all proportions as well as isotopic forms such as deuterated compounds.

Suitable salts of the compounds of formula I include acid addition salts such as those with an inorganic acid such as hydrochloric, hydrobromic, sulphuric, nitric or phosphoric acid, or an organic carboxylic acid such as oxalic, tartaric, lactic, butyric, toluic, hexanoic or phthalic acid, or a sulphonic acid such as methane, benzene or toluene sulphonic acid. Other examples of organic carboxylic acids include haloacids such as trifluoroacetic acid.

N-oxides are oxidised forms of tertiary amines or oxidised forms of nitrogen containing heteroaromatic compounds. They are described in many books for example in "Heterocyclic N-oxides" by Angelo Albini and Silvio Pietra, CRC Press, Boca Raton, Fla., 1991.

In particularly preferred embodiments of the invention, the preferred groups for X, Y and $R^1$ to $R^5$, in any combination thereof, are as set out below.

In one embodiment, X is S and Y is N (compounds of formula Ia):

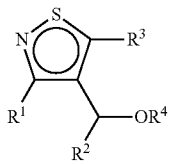

Ia

In another embodiment, X is $NR^5$ and Y is N (compounds of formula Ib):

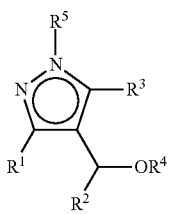

Ib

In another embodiment, X is N and Y is $NR^5$ (compounds of formula Ic):

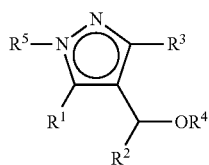

Ic

In one embodiment, $R^1$ and $R^3$ are, independently, hydrogen or optionally substituted alkyl, alkenyl, alkynyl, heterocyclyl or trialkylsilyl.

Alkyl, alkenyl, alkynyl and trialkylsilyl groups are as defined above. In particular, alkyl groups include methyl, ethyl, iso-propyl, butyl, iso-butyl, iso-amyl and cyclohexyl groups.

In another embodiment, $R^1$ and $R^3$ are, independently, hydrogen or optionally substituted alkyl, aryloxyalkyl, arylthioalkyl, aryl or heteroaryl.

Aryl groups are as defined above. In particular, aryl groups include benzyl or phenyl groups optionally substituted with one or more (in particular, one or two) of the same or different halogen atoms (for example chloro and fluoro), haloalkyl or haloalkoxy groups. For example, aryl groups include benzyl, phenyl, 2-chlorophenyl, 3-chlorophenyl, 4-chlorophenyl, 2,4-dichlorophenyl, 2-fluorophenyl, 3-fluorophenyl, 4-fluorophenyl, 2-fluoro-4-chlorophenyl, 2,4-dichlorophenyl, 2,4-difluorophenyl, 3,5-difluorophenyl, 3-trifluoromethylphenyl, 4-trifluoromethylphenyl and 4-trifluoromethoxyphenyl.

Heteroaryl groups are as defined above. In particular, heteroaryl groups include 5- or 6-membered heteroaryl rings such as furyl and thienyl rings. These heteroaryl groups may be optionally substituted by one or more (in particular, one or two) of the same of different halogen atoms and include, for example, 2-furyl, 3-furyl, 2-thienyl, 3-thienyl, 5-chloro-2-thienyl, or 5-chloro-2-furyl.

In another embodiment, $R^1$ and $R^3$ are, independently, hydrogen or optionally substituted alkyl, phenyl or 5- or 6-membered heteroaryl.

In one embodiment, $R^2$ is optionally substituted heteroaryl. Heteroaryl is as defined above and, in particular, is pyridyl, pyrimidinyl or thiazolyl optionally substituted with one or more (in particular, one or two) of the same or different halogen, alkyl or alkoxy groups. Examples include 2-pyridyl, 3-pyridyl, 4-pyridyl, 3-pyrimidinyl, 5-pyrimidinyl, 4-fluoro-3-pyridyl, 4-methyl-3-pyridyl, 5-methoxy-3-pyridyl, 4-methyl-5-pyrimidinyl, 4-methoxy-5-pyrimidinyl, 2-thiazolyl or 5-thiazolyl.

In one embodiment, $R^4$ is hydrogen or acyl.

Acyl groups are as defined above. In particular, acyl groups include methylcarbonyl, ethylcarbonyl or cyclopropylcarbonyl.

In another embodiment $R^4$ is hydrogen.

In one embodiment, $R^5$ is hydrogen or optionally substituted alkyl, alkenyl or alkynyl.

Alkyl, alkenyl and alkynyl groups are as defined above. In particular, these groups contain from 1 to 4 carbon atoms and include methyl, ethyl, iso-propyl, butyl, iso-butyl and cyclopropyl.

In another embodiment, $R^5$ is hydrogen or optionally substituted trialkylsilyl or arylalkyl. Trialkylsilyl and arylalkyl groups are as defined above.

In another embodiment, $R^5$ is hydrogen or optionally substituted aryl or heteroaryl.

Aryl groups are as defined above. In particular, aryl groups include phenyl and optionally substituted phenyl groups. Heteroaryl groups are as defined above.

In one embodiment, at least one of $R^1$, $R^3$ and $R^5$ is not hydrogen, the other groups, X, Y and $R^2$ and $R^4$ being as defined above.

In one embodiment, $R^1$ is optionally substituted alkyl, alkenyl, alkynyl, heterocyclyl, trialkylsilyl, arylalkyl, aryloxyalkyl, arylthioalkyl, aryl or heteroaryl; $R^3$ is hydrogen; and X, Y, $R^2$, $R^4$ and $R^5$ (where $R^5$ exists) are as described in any embodiment above.

In one embodiment, $R^1$ is hydrogen; $R^3$ is optionally substituted alkyl, alkenyl, alkynyl, heterocyclyl, trialkylsilyl arylalkyl, aryloxyalkyl, arylthioalkyl, aryl or heteroaryl; and X, Y, $R^2$, $R^4$ and $R^5$ (where $R^5$ exists) are as described in any embodiment above.

In one embodiment, $R^1$ is optionally substituted aryloxyalkyl, arylthioalkyl, aryl or heteroaryl; $R^3$ is hydrogen, optionally substituted alkyl, alkenyl, alkynyl, heterocyclyl or trialkylsilyl; and X, Y, $R^2$, $R^4$ and $R^5$ (where $R^5$ exists) are as described in any embodiment above.

In one embodiment, $R^1$ is hydrogen, optionally substituted alkyl, alkenyl, alkynyl, heterocyclyl or trialkylsilyl; $R^3$ is optionally substituted aryloxyalkyl, arylthioalkyl, aryl or heteroaryl; and X, Y, $R^2$, $R^4$ and $R^5$ (where $R^5$ exists) are as described in any embodiment above.

In one embodiment, the present invention provides a compound of formula I:

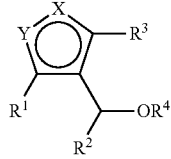

wherein
X is S and Y is N;
R$^1$ and R$^3$ are, independently, optionally substituted aryl or heteroaryl;
R$^2$ is optionally substituted aryl or heteroaryl; and
R$^4$ is hydrogen or acyl.

Preferred subgroups of compounds of formula I according to the invention are those wherein:
X is S and Y is N;
R$^1$ is optionally substituted phenyl or thienyl;
R$^2$ is optionally substituted pyridyl or pyrimidinyl;
R$^3$ is optionally substituted phenyl; and
R$^4$ is hydrogen.

Most referred subgroups of compounds of formula I according to the invention are those wherein:
X is S and Y is N;
R$^1$ is 3-chloro-phenyl, 4-chloro-phenyl, 2-fluoro-phenyl, 2,4-difluoro-phenyl or 2-thienyl;
R$^2$ is 3-pyridyl or 3-pyrimidinyl;
R$^3$ is phenyl, 4-chloro-phenyl, 2,4-dichloro-phenyl, 4-bromo-phenyl, 2-fluoro-4-chloro-phenyl; and
R$^4$ is hydrogen.

In one embodiment, the present invention provides a compound of formula I:

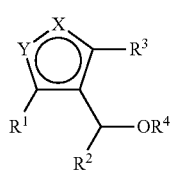

wherein
X is NR$^5$ and Y is N;
R$^1$ and R$^3$ are, independently, optionally substituted aryl or heteroaryl;
R$^2$ is optionally substituted aryl or heteroaryl;
R$^4$ is hydrogen or acyl; and
R$^5$ is hydrogen or optionally substituted alkyl, arylalkyl, aryloxyalkyl or aryl.

Preferred subgroups of compounds of formula I according to the invention are those wherein:
X is NR$^5$ and Y is N;
R$^1$ and R$^3$ are optionally substituted aryl;
R$^2$ is optionally substituted heteroaryl;
R$^4$ is hydrogen; and
R$^5$ is hydrogen or optionally substituted alkyl, arylalkyl or phenyl.

Most preferred subgroups of compounds of formula I according to the invention are those wherein:
X is NR$^5$ and Y is N;
R$^1$ is 4-chloro-phenyl, 4-bromo-phenyl, 2-fluoro-phenyl, 3-fluoro-phenyl, 4-fluoro-phenyl or 2,4-difluoro-phenyl;
R$^2$ is 3-pyridyl;
R$^3$ is 4-methoxy-phenyl, 4-chloro-phenyl or 2,4-difluoro-phenyl;
R$^4$ is hydrogen; and
R$^5$ is methyl or benzyl.

In one embodiment, the present invention provides a compound of formula I:

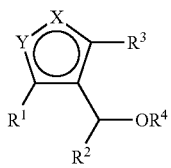

wherein
X is N and Y is NR$^5$;
R$^1$ and R$^3$ are, independently, optionally substituted aryl or heteroaryl;
R$^2$ is optionally substituted aryl or heteroaryl;
R$^4$ is hydrogen or acyl; and
R$^5$ is hydrogen, optionally substituted alkyl or aryl.

Preferred subgroups of compounds of formula I according to the invention are those wherein:
X is N and Y is NR$^5$;
R$^1$ and R$^3$ are optionally substituted aryl;
R$^2$ is optionally substituted heteroaryl;
R$^4$ is hydrogen; and
R$^5$ is hydrogen or optionally substituted alkyl.

Most preferred subgroups of compounds of formula I according to the invention are those wherein:
X is N and Y is NR$^5$;
R$^1$ is 4-chloro-phenyl, 2-fluoro-phenyl, 3-fluoro-phenyl or 2,4-difluoro-phenyl;
R$^2$ is 3-pyridyl;
R$^3$ is 4-chloro-phenyl or 4-fluoro-phenyl;
R$^4$ is hydrogen; and
R$^5$ is methyl.

In one embodiment, R$^1$ is optionally substituted aryl or heteroaryl; R$^3$ is hydrogen or optionally substituted alkyl; and X, Y, R$^2$, R$^4$ and R$^5$ (where R$^5$ exists) are as described in any embodiment above.

In one embodiment, R$^1$ is hydrogen or optionally substituted alkyl; R$^3$ is optionally substituted aryl or heteroaryl; and X, Y, R$^2$, R$^4$ and R$^5$ (where R$^5$ exists) are as described in any embodiment above.

In one embodiment, R$^1$ is optionally substituted phenyl or 5- or 6-membered heteroaryl; R$^3$ is hydrogen, optionally substituted alkyl, alkenyl, alkynyl or heterocyclyl; and X, Y, R$^2$, R$^4$ and R$^5$ (where R$^5$ exists) are as described in any embodiment above.

In one embodiment, R$^1$ is hydrogen, optionally substituted alkyl, alkenyl, alkynyl or heterocyclyl; R$^3$ is optionally substituted phenyl or 5- or 6-membered heteroaryl; and X, Y, R$^2$, R$^4$ and R$^5$ (where R$^5$ exists) are as described in any embodiment above.

More particularly, compounds for use in the present invention are shown in Table I (compounds of formula Ia), Table II (compounds of formula Ib) and Table III (compounds of formula Ic) below:

TABLE I

Ia

| No | R¹ | R² | R³ | R⁴ | Melting point or Mass peak(s) of MS |
|---|---|---|---|---|---|
| A1 | 4-Cl—Ph | 3-Py | Ph | H | 379/381 |
| A2 | 4-Cl—Ph | 3-Py | 4-Cl—Ph | H | 413/415 |
| A3 | 4-Cl—Ph | 3-Py | 4-Cl—Ph | C(O)Me | |
| A4 | 3-Cl—Ph | 3-Py | Ph | H | 379/381 |
| A5 | 4-Cl—Ph | 3-Py | 2-Cl—Ph | H | |
| A6 | 4-Cl—Ph | 3-Py | 5-Cl, 2-Thioph | H | |
| A7 | 4-Cl—Ph | 3-Py | 3-Cl—Ph | H | |
| A8 | 4-Cl—Ph | 3-Py | 5-Br, 2-Thioph | H | |
| A9 | 2,4-Cl₂—Ph | 3-Py | 3-Cl—Ph | C(O)Et | |
| A10 | 2,4-Cl₂—Ph | 3-Py | 4-Cl—Ph | H | |
| A11 | 2,4-Cl₂—Ph | 3-Py | Ph | H | |
| A12 | 2,4-Cl₂—Ph | 3-Py | 2-Cl—Ph | H | |
| A13 | 2,4-Cl₂—Ph | 3-Py | 3-Cl—Ph | H | |
| A14 | 4-Cl—Ph | 3-Py | 2,4-Cl₂—Ph | H | 447/449 |
| A15 | 2-Cl—Ph | 3-Py | 2,4-Cl₂—Ph | H | |
| A16 | 3-Cl—Ph | 3-Py | 2,4-Cl₂—Ph | H | 447/449 |
| A17 | 4-Cl—Ph | 5-Pyrimi | 4-Cl—Ph | H | |
| A18 | 4-Cl—Ph | 5-Pyrimi | 2-Cl—Ph | H | |
| A19 | 4-Cl—Ph | 5-Pyrimi | 3-Cl—Ph | H | |
| A20 | 2,4-Cl₂—Ph | 5-Pyrimi | 4-Cl—Ph | H | |
| A21 | 2,4-Cl₂—Ph | 5-Pyrimi | 2-Cl—Ph | H | |
| A22 | 2,4-Cl₂—Ph | 5-Pyrimi | 3-Cl—Ph | H | |
| A23 | 4-Cl—Ph | 5-Pyrimi | 2,4-Cl₂—Ph | H | |
| A24 | 2-Cl—Ph | 5-Pyrimi | 2,4-Cl₂—Ph | H | |
| A25 | 3-Cl—Ph | 5-Pyrimi | 2,4-Cl₂—Ph | H | |
| A26 | 2-F,4-Cl—Ph | 5-Pyrimi | 4-Cl—Ph | H | |
| A27 | 2-F,4-Cl—Ph | 5-Pyrimi | 2-Cl—Ph | H | |
| A28 | 2-F,4-Cl—Ph | 5-Pyrimi | 3-Cl—Ph | H | |
| A29 | 2-F,4-Cl—Ph | 3-Py | 4-Cl—Ph | H | |
| A30 | 2-F,4-Cl—Ph | 3-Py | 2-Cl—Ph | H | |
| A31 | 2-F,4-Cl—Ph | 3-Py | 3-Cl—Ph | H | |
| A32 | 2,4-F₂—Ph | 5-Pyrimi | 4-Cl—Ph | H | |
| A33 | 2,4-F₂—Ph | 5-Pyrimi | 2-Cl—Ph | H | |
| A34 | 2,4-F₂—Ph | 5-Pyrimi | 3-Cl—Ph | H | |
| A35 | 4-Cl—Ph | 4-F, 3-Py | 2,4-Cl₂—Ph | H | |
| A36 | 2-Cl—Ph | 4-Me, 3-Py | 2,4-Cl₂—Ph | H | |
| A37 | 3-Cl—Ph | 4-MeO, 3-Py | 2,4-Cl₂—Ph | H | |
| A38 | 4-Cl—Ph | 3-Py | 2,4-Cl₂—Ph | C(O)-c-Prop | |
| A39 | 2-Cl—Ph | 3-Py | 2,4-Cl₂—Ph | H | |
| A40 | 3-Cl—Ph | 3-Py | 5-Cl, 2-Thioph | H | |
| A41 | 4-Cl—Ph | 4-Me, 5-Pyrimi | 4-Cl—Ph | H | |
| A42 | 4-Cl—Ph | 4-MeO, 5-Pyrimi | 2-Cl—Ph | H | |
| A43 | 4-Cl—Ph | 5-Pyrimi | 3-CF₃—Ph | H | |
| A44 | 2-Thioph | 3-Py | 4-Cl—Ph | H | 172-173° C. |
| A45 | 4-Cl—Ph | 3-Py | 2-Thioph | H | |
| A46 | 2-Fur | 3-Py | 2,4-Cl₂—Ph | H | |
| A47 | 2,4-Cl₂—Ph | 3-Py | 2-Fur | H | |
| A48 | 3-Fur | 3-Py | 2,4-Cl₂—Ph | H | |
| A49 | 2,4-Cl₂—Ph | 3-Py | 3-Fur | H | |
| A50 | c-Hx | 3-Py | 4-Cl—Ph | H | |
| A51 | c-Hx | 3-Py | 2,4-F₂—Ph | H | |
| A52 | 2-Cl—Ph | 3-Py | c-Hx | H | |
| A53 | 2,4-Cl₂—Ph | 3-Py | c-Hx | H | |
| A54 | i-Prop | 3-Py | 4-Cl—Ph | H | |
| A55 | 2,4-Cl₂—Ph | 3-Py | i-Prop | H | |
| A56 | 2,4-Cl₂—Ph | 3-Py | i-Amyl | H | |
| A57 | 4-Cl—Ph | 3-Py | Et | H | |
| A58 | 4-Br—Ph | 3-Py | 4-Cl—Ph | H | |
| A59 | 2,4-Cl₂—Ph | 3-Py | 4-Cl—Ph | C(O)Me | |
| A60 | Bn | 3-Py | 4-Cl—Ph | H | |
| A61 | 2,4-Cl₂—Ph | 3-Py | 4-Br—Ph | H | |
| A62 | 2-Thioph | 3-Py | Ph | H | 351 |
| A63 | 2-Thioph | 3-Py | 2,4-Cl₂—Ph | H | 419/421 |
| A64 | 2-Thioph | 3-Py | 4-Br—Ph | H | 187-188° C. |
| A65 | 2-F—Ph | 3-Py | 4-Cl—Ph | H | 186-187° C. |
| A66 | 2-F—Ph | 3-Py | Ph | H | 363 |

TABLE I-continued

Ia

| No | $R^1$ | $R^2$ | $R^3$ | $R^4$ | Melting point or Mass peak(s) of MS |
|---|---|---|---|---|---|
| A67 | 2-F—Ph | 3-Py | 2,4-$Cl_2$—Ph | H | 182-183° C. |
| A68 | 2-F—Ph | 3-Py | 4-Br—Ph | H | 414/443 |
| A69 | 4-Cl—Ph | 3-Py | 4-Br—Ph | H | 457/459 |
| A70 | 4-Cl—Ph | 3-Py | 2-F, 4-Cl—Ph | H | 431/433 |
| A71 | 2-Thioph | 3-Py | 2-F, 4-Cl—Ph | H | 403/405 |
| A72 | 2-F—Ph | 3-Py | 2-F, 4-Cl—Ph | H | 415/417 |
| A73 | 3-Cl—Ph | 3-Py | 4-Cl—Ph | H | 413/415 |
| A74 | 3-Cl—Ph | 3-Py | 4-Br—Ph | H | 457/459 |
| A75 | 3-Cl—Ph | 3-Py | 2-F, 4-Cl—Ph | H | 431/433 |
| A76 | 2,4-$F_2$—Ph | 3-Py | Ph | H | 381/382 |
| A77 | 2,4-$F_2$—Ph | 3-Py | 4-Cl—Ph | H | 415/417 |
| A78 | 2,4-$F_2$—Ph | 3-Py | 4-Br—Ph | H | 459/461 |
| A79 | 2,4-$F_2$—Ph | 3-Py | 2,4-$Cl_2$—Ph | H | 449/451 |
| A80 | 2,4-$F_2$—Ph | 3-Py | 2-F, 4-Cl—Ph | H | 433/435 |
| A81 | 2,4-$F_2$—Ph | 3-Pyrimi | 2-F, 4-Cl—Ph | H | 184-185° C. |

TABLE II

Ib

| No | $R^1$ | $R^2$ | $R^3$ | $R^4$ | $R^5$ | Melting point or Mass peak(s) of MS |
|---|---|---|---|---|---|---|
| B1 | 4-Cl—Ph | 3-Py | Ph | H | H | |
| B2 | 4-Cl—Ph | 3-Py | 4-Cl—Ph | H | H | |
| B3 | 4-Cl—Ph | 3-Py | 4-Cl—Ph | C(O)Me | Me | |
| B4 | 3-Cl—Ph | 3-Py | Ph | H | Me | |
| B5 | 4-Cl—Ph | 3-Py | 2-Cl—Ph | H | Me | |
| B6 | 4-Cl—Ph | 3-Py | 5-Cl, 2-Thioph | H | Me | |
| B7 | 4-Cl—Ph | 3-Py | 3-Cl—Ph | H | Me | |
| B8 | 4-Cl—Ph | 3-Py | 5-Br, 2-Thioph | H | Me | |
| B9 | 2,4-$Cl_2$—Ph | 3-Py | 3-Cl—Ph | C(O)Et | Me | |
| B10 | 2,4-$Cl_2$—Ph | 3-Py | 4-Cl—Ph | H | Me | |
| B11 | 2,4-$Cl_2$—Ph | 3-Py | Ph | H | Me | |
| B12 | 2,4-$Cl_2$—Ph | 3-Py | 2-Cl—Ph | H | Me | |
| B13 | 2,4-$Cl_2$—Ph | 3-Py | 3-Cl—Ph | H | Me | |
| B14 | 4-Cl—Ph | 3-Py | 2,4-$Cl_2$—Ph | H | Me | |
| B15 | 2-Cl—Ph | 3-Py | 2,4-$Cl_2$—Ph | H | Me | |
| B16 | 3-Cl—Ph | 3-Py | 2,4-$Cl_2$—Ph | H | Me | |
| B17 | 4-Cl—Ph | 5-Pyrimi | 4-Cl—Ph | H | Me | |
| B18 | 4-Cl—Ph | 5-Pyrimi | 2-Cl—Ph | H | Me | |
| B19 | 4-Cl—Ph | 5-Pyrimi | 3-Cl—Ph | H | Me | |
| B20 | 2,4-$Cl_2$—Ph | 5-Pyrimi | 4-Cl—Ph | H | Me | |
| B21 | 2,4-$Cl_2$—Ph | 5-Pyrimi | 2-Cl—Ph | H | Me | |
| B22 | 2,4-$Cl_2$—Ph | 5-Pyrimi | 3-Cl—Ph | H | Me | |
| B23 | 4-Cl—Ph | 5-Pyrimi | 2,4-$Cl_2$—Ph | H | Me | |
| B24 | 2-Cl—Ph | 5-Pyrimi | 2,4-$Cl_2$—Ph | H | Me | |
| B25 | 3-Cl—Ph | 5-Pyrimi | 2,4-$Cl_2$—Ph | H | Me | |
| B26 | 2-F,4-Cl—Ph | 5-Pyrimi | 4-Cl—Ph | H | Me | |
| B27 | 2-F,4-Cl—Ph | 5-Pyrimi | 2-Cl—Ph | H | Me | |
| B28 | 2-F,4-Cl—Ph | 5-Pyrimi | 3-Cl—Ph | H | Me | |
| B29 | 2-F,4-Cl—Ph | 3-Py | 4-Cl—Ph | H | Me | |
| B30 | 2-F,4-Cl—Ph | 3-Py | 2-Cl—Ph | H | Me | |

TABLE II-continued

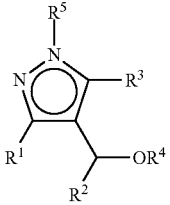

Ib

| No | R¹ | R² | R³ | R⁴ | R⁵ | Melting point or Mass peak(s) of MS |
|---|---|---|---|---|---|---|
| B31 | 2-F,4-Cl—Ph | 3-Py | 3-Cl—Ph | H | Me | |
| B32 | 2,4-F₂—Ph | 5-Pyrimi | 4-Cl—Ph | H | Me | |
| B33 | 2,4-F₂—Ph | 5-Pyrimi | 2-Cl—Ph | H | Me | |
| B34 | 2,4-F₂—Ph | 5-Pyrimi | 3-Cl—Ph | H | Me | |
| B35 | 4-Cl—Ph | 4-F, 3-Py | 2,4-Cl₂—Ph | H | Me | |
| B36 | 2-Cl—Ph | 4-Me, 3-Py | 2,4-Cl₂—Ph | H | Me | |
| B37 | 3-Cl—Ph | 4-MeO, 3-Py | 2,4-Cl₂—Ph | H | Me | |
| B38 | 4-Cl—Ph | 3-Py | 2,4-Cl₂—Ph | C(O)-c-Prop | Me | |
| B39 | 2-Cl—Ph | 3-Py | 2,4-Cl₂—Ph | H | Me | |
| B40 | 3-Cl—Ph | 3-Py | 5-Cl, 2-Thioph | H | Me | |
| B41 | 4-Cl—Ph | 4-Me, 5-Pyrimi | 4-Cl—Ph | H | Me | |
| B42 | 4-Cl—Ph | 4-MeO,5-Pyrimi | 2-Cl—Ph | H | Me | |
| B43 | 4-Cl—Ph | 5-Pyrimi | 3-CF₃—Ph | H | Me | |
| B44 | 2-Thioph | 3-Py | 4-Cl—Ph | H | Me | |
| B45 | 4-Cl—Ph | 3-Py | 2-Thioph | H | Me | |
| B46 | 2-Fur | 3-Py | 2,4-Cl₂—Ph | H | Me | |
| B47 | 2,4-Cl₂—Ph | 3-Py | 2-Fur | H | Me | |
| B48 | 3-Fur | 3-Py | 2,4-Cl₂—Ph | H | Me | |
| B49 | 2,4-Cl₂—Ph | 3-Py | 3-Fur | H | Me | |
| B50 | c-Hx | 3-Py | 4-Cl—Ph | H | Me | |
| B51 | c-Hx | 3-Py | 2,4-F₂—Ph | H | Me | |
| B52 | 2-Cl—Ph | 3-Py | c-Hx | H | Me | |
| B53 | 2,4-Cl₂—Ph | 3-Py | c-Hx | H | Me | |
| B54 | i-Prop | 3-Py | 4-Cl—Ph | H | Me | |
| B55 | 2,4-Cl₂—Ph | 3-Py | i-Prop | H | Me | |
| B56 | 2,4-Cl₂—Ph | 3-Py | i-Amyl | H | Me | |
| B57 | 4-Cl—Ph | 3-Py | Et | H | Me | |
| B58 | 4-Br—Ph | 3-Py | 4-Cl—Ph | H | Me | |
| B59 | 2,4-Cl₂—Ph | 3-Py | 4-Cl—Ph | C(O)Me | Me | |
| B60 | Bn | 3-Py | 4-Cl—Ph | H | Me | |
| B61 | 2,4-Cl₂—Ph | 3-Py | 4-Br—Ph | H | Me | |
| B62 | 4-Cl—Ph | 3-Py | Ph | H | Me | |
| B63 | 4-Cl—Ph | 3-Py | Ph | H | Ph | |
| B64 | 4-Cl—Ph | 3-Py | 4-Cl—Ph | C(O)Me | Et | |
| B65 | 4-Cl—Ph | 3-Py | 3-Cl—Ph | H | H | |
| B66 | 4-Cl—Ph | 3-Py | 3-Cl—Ph | H | Et | |
| B67 | 4-Cl—Ph | 3-Py | 3-Cl—Ph | H | c-Prop | |
| B68 | 3-Cl—Ph | 3-Py | 4-Cl—Ph | H | H | |
| B69 | 4-Cl—Ph | 3-Py | 3-Cl—Ph | H | i-Prop | |
| B70 | 3-Cl—Ph | 3-Py | 4-Cl—Ph | H | Me | |
| B71 | 3-Cl—Ph | 3-Py | 4-Cl—Ph | H | Ph | |
| B72 | 2,4-Cl₂—Ph | 3-Py | 4-Cl—Ph | H | H | |
| B73 | 2,4-Cl₂—Ph | 3-Py | Ph | H | H | |
| B74 | 2,4-Cl₂—Ph | 3-Py | 2-Cl—Ph | H | H | |
| B75 | 2,4-Cl₂—Ph | 3-Py | 3-Cl—Ph | H | H | |
| B76 | 2-F,4-Cl—Ph | 5-Pyrimi | 4-Cl—Ph | H | H | |
| B77 | 2-F,4-Cl—Ph | 5-Pyrimi | 2-Cl—Ph | H | H | |
| B78 | 2-F,4-Cl—Ph | 5-Pyrimi | 3-Cl—Ph | H | H | |
| B79 | 2-F,4-Cl—Ph | 3-Py | 4-Cl—Ph | H | H | |
| B80 | 4-Cl—Ph | 5-Pyrimi | 2-F, 4-Cl—Ph | H | H | |
| B81 | 2-Cl—Ph | 5-Pyrimi | 2-F, 4-Cl—Ph | H | H | |
| B82 | 3-Cl—Ph | 5-Pyrimi | 2-F, 4-Cl—Ph | H | H | |
| B83 | 4-Cl—Ph | 3-Py | 2-F, 4-Cl—Ph | H | H | |
| B84 | 4-Br—Ph | 3-Py | 4-OMe—Ph | H | Me | 450/452 |
| B85 | 4-Cl—Ph | 3-Py | 4-Cl—Ph | H | Me | 410/412 |
| B86 | 2,4-F₂—Ph | 3-Py | 2,4-F₂—Ph | H | Me | 199-200° C. |
| B87 | 4-Cl—Ph | 3-Py | 2,4-F₂—Ph | H | Me | 117-119° C. |
| B88 | 4-F—Ph | 3-Py | 4-Cl—Ph | H | Me | 394/396 |
| B89 | 3-F—Ph | 3-Py | 4-Cl—Ph | H | Me | 394/396 |
| B90 | 2-F—Ph | 3-Py | 4-Cl—Ph | H | Me | 394/396 |
| B91 | 4-Cl—Ph | 3-Py | 4-Cl—Ph | H | Bn | 486/488 |

TABLE III

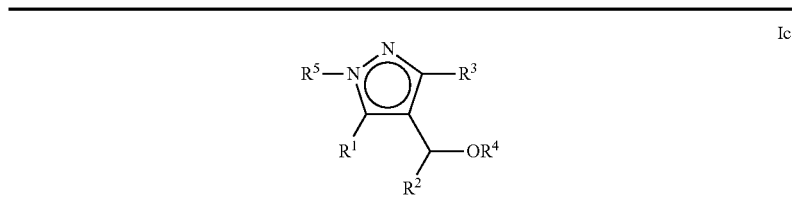

Ic

| No | R¹ | R² | R³ | R⁴ | R⁵ | Melting point or Mass peak(s) of MS |
|---|---|---|---|---|---|---|
| C1 | 4-Cl—Ph | 3-Py | Ph | H | H | |
| C2 | 4-Cl—Ph | 3-Py | 4-Cl—Ph | H | H | |
| C3 | 4-Cl—Ph | 3-Py | 4-Cl—Ph | C(O)Me | Me | |
| C4 | 3-Cl—Ph | 3-Py | Ph | H | Me | |
| C5 | 4-Cl—Ph | 3-Py | 2-Cl—Ph | H | Me | |
| C6 | 4-Cl—Ph | 3-Py | 5-Cl, 2-Thioph | H | Me | |
| C7 | 4-Cl—Ph | 3-Py | 3-Cl—Ph | H | Me | |
| C8 | 4-Cl—Ph | 3-Py | 5-Br, 2-Thioph | H | Me | |
| C9 | 2,4-Cl₂—Ph | 3-Py | 3-Cl—Ph | C(O)Et | Me | |
| C10 | 2,4-Cl₂—Ph | 3-Py | 4-Cl—Ph | H | Me | |
| C11 | 2,4-Cl₂—Ph | 3-Py | Ph | H | Me | |
| C12 | 2,4-Cl₂—Ph | 3-Py | 2-Cl—Ph | H | Me | |
| C13 | 2,4-Cl₂—Ph | 3-Py | 3-Cl—Ph | H | Me | |
| C14 | 4-Cl—Ph | 3-Py | 2,4-Cl₂—Ph | H | Me | |
| C15 | 2-Cl—Ph | 3-Py | 2,4-Cl₂—Ph | H | Me | |
| C16 | 3-Cl—Ph | 3-Py | 2,4-Cl₂—Ph | H | Me | |
| C17 | 4-Cl—Ph | 5-Pyrimi | 4-Cl—Ph | H | Me | |
| C18 | 4-Cl—Ph | 5-Pyrimi | 2-Cl—Ph | H | Me | |
| C19 | 4-Cl—Ph | 5-Pyrimi | 3-Cl—Ph | H | Me | |
| C20 | 2,4-Cl₂—Ph | 5-Pyrimi | 4-Cl—Ph | H | Me | |
| C21 | 2,4-Cl₂—Ph | 5-Pyrimi | 2-Cl—Ph | H | Me | |
| C22 | 2,4-Cl₂—Ph | 5-Pyrimi | 3-Cl—Ph | H | Me | |
| C23 | 4-Cl—Ph | 5-Pyrimi | 2,4-Cl₂—Ph | H | Me | |
| C24 | 2-Cl—Ph | 5-Pyrimi | 2,4-Cl₂—Ph | H | Me | |
| C25 | 3-Cl—Ph | 5-Pyrimi | 2,4-Cl₂—Ph | H | Me | |
| C26 | 2-F, 4-Cl₂—Ph | 5-Pyrimi | 4-Cl—Ph | H | Me | |
| C27 | 2-F, 4-Cl₂—Ph | 5-Pyrimi | 2-Cl—Ph | H | Me | |
| C28 | 2-F, 4-Cl₂—Ph | 5-Pyrimi | 3-Cl—Ph | H | Me | |
| C29 | 2-F, 4-Cl₂—Ph | 3-Py | 4-Cl—Ph | H | Me | |
| C30 | 2-F, 4-Cl₂—Ph | 3-Py | 2-Cl—Ph | H | Me | |
| C31 | 2-F, 4-Cl₂—Ph | 3-Py | 3-Cl—Ph | H | Me | |
| C32 | 2,4-F₂—Ph | 5-Pyrimi | 4-Cl—Ph | H | Me | |
| C33 | 2,4-F₂—Ph | 5-Pyrimi | 2-Cl—Ph | H | Me | |
| C34 | 2,4-F₂—Ph | 5-Pyrimi | 3-Cl—Ph | H | Me | |
| C35 | 4-Cl—Ph | 4-F, 3-Py | 2,4-Cl₂—Ph | H | Me | |
| C36 | 2-Cl—Ph | 4-Me, 3-Py | 2,4-Cl₂—Ph | H | Me | |
| C37 | 3-Cl—Ph | 5-MeO, 3-Py | 2,4-Cl₂—Ph | H | Me | |
| C38 | 4-Cl—Ph | 3-Py | 2,4-Cl₂—Ph | C(O)-c-Prop | Me | |
| C39 | 2-Cl—Ph | 3-Py | 2,4-Cl₂—Ph | H | Me | |
| C40 | 3-Cl—Ph | 3-Py | 5-Cl, 2-Thioph | H | Me | |
| C41 | 4-Cl—Ph | 4-Me, 5-Pyrimi | 4-Cl—Ph | H | Me | |
| C42 | 4-Cl—Ph | 4-Meo, 5-Pyrimi | 2-Cl—Ph | H | Me | |
| C43 | 4-Cl—Ph | 5-Pyrimi | 3-CF₃—Ph | H | Me | |
| C44 | 2-Thioph | 3-Py | 4-Cl—Ph | H | Me | |
| C45 | 4-Cl—Ph | 3-Py | 2-Thioph | H | Me | |
| C46 | 2-Fur | 3-Py | 2,4-Cl₂—Ph | H | Me | |
| C47 | 2,4-Cl₂—Ph | 3-Py | 2-Fur | H | Me | |
| C48 | 3-Fur | 3-Py | 2,4-Cl₂—Ph | H | Me | |
| C49 | 2,4-Cl₂—Ph | 3-Py | 3-Fur | H | Me | |
| C50 | c-Hx | 3-Py | 4-Cl—Ph | H | Me | |
| C51 | c-Hx | 3-Py | 2,4-F₂—Ph | H | Me | |
| C52 | 2-Cl—Ph | 3-Py | c-Hx | H | Me | |
| C53 | 2,4-Cl₂—Ph | 3-Py | c-Hx | H | Me | |
| C54 | i-Prop | 3-Py | 4-Cl—Ph | H | Me | |
| C55 | 2,4-Cl₂—Ph | 3-Py | i-Prop | H | Me | |
| C56 | 2,4-Cl₂—Ph | 3-Py | i-Amyl | H | Me | |
| C57 | 4-Cl—Ph | 3-Py | Et | H | Me | |
| C58 | 4-Br—Ph | 3-Py | 4-Cl—Ph | H | Me | |
| C59 | 2,4-Cl₂—Ph | 3-Py | 4-Cl—Ph | C(O)Me | Me | |
| C60 | Bn | 3-Py | 4-Cl—Ph | H | Me | |
| C61 | 2,4-Cl₂—Ph | 3-Py | 4-Br—Ph | H | Me | |
| C62 | 4-Cl—Ph | 3-Py | Ph | H | Me | |
| C63 | 4-Cl—Ph | 3-Py | Ph | H | Ph | |
| C64 | 4-Cl—Ph | 3-Py | 4-Cl—Ph | C(O)Me | Et | |
| C65 | 4-Cl—Ph | 3-Py | 3-Cl—Ph | H | H | |
| C66 | 4-Cl—Ph | 3-Py | 3-Cl—Ph | H | Et | |

TABLE III-continued

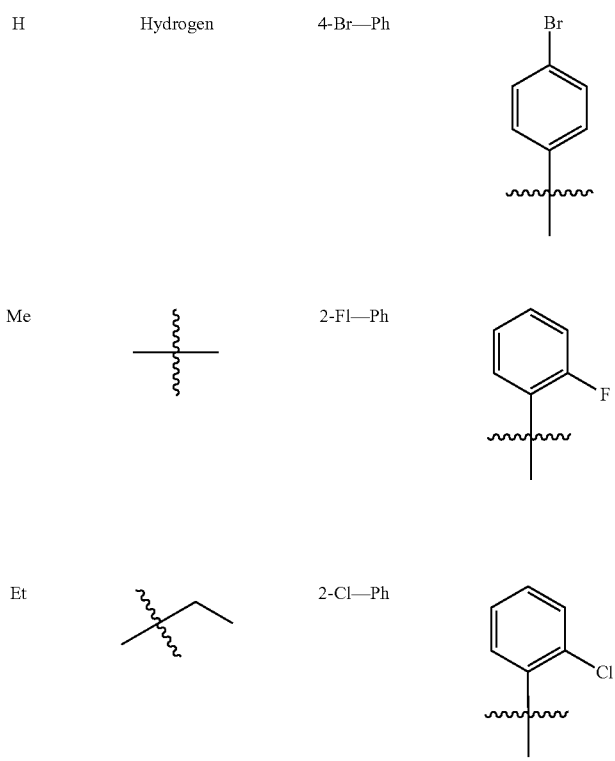

Ic

| No | R¹ | R² | R³ | R⁴ | R⁵ | Melting point or Mass peak(s) of MS |
|---|---|---|---|---|---|---|
| C67 | 4-Cl—Ph | 3-Py | 3-Cl—Ph | H | c-Prop | |
| C68 | 3-Cl—Ph | 3-Py | 4-Cl—Ph | H | H | |
| C69 | 4-Cl—Ph | 3-Py | 3-Cl—Ph | H | i-Prop | |
| C70 | 3-Cl—Ph | 3-Py | 4-Cl—Ph | H | Me | |
| C71 | 3-Cl—Ph | 3-Py | 4-Cl—Ph | H | Ph | |
| C72 | 2,4-Cl₂—Ph | 3-Py | 4-Cl—Ph | H | H | |
| C73 | 2,4-Cl₂—Ph | 3-Py | Ph | H | H | |
| C74 | 2,4-Cl₂—Ph | 3-Py | 2-Cl—Ph | H | H | |
| C75 | 2,4-Cl₂—Ph | 3-Py | 3-Cl—Ph | H | H | |
| C76 | 2-F, 4-Cl—Ph | 5-Pyrimi | 4-Cl—Ph | H | H | |
| C77 | 2-F, 4-Cl—Ph | 5-Pyrimi | 2-Cl—Ph | H | H | |
| C78 | 2-F, 4-Cl—Ph | 5-Pyrimi | 3-Cl—Ph | H | H | |
| C79 | 2-F, 4-Cl—Ph | 3-Py | 4-Cl—Ph | H | H | |
| C80 | 4-Cl—Ph | 5-Pyrimi | 2-F, 4-Cl—Ph | H | H | |
| C81 | 2-Cl—Ph | 5-Pyrimi | 2-F, 4-Cl—Ph | H | H | |
| C82 | 3-Cl—Ph | 5-Pyrimi | 2-F, 4-Cl—Ph | H | H | |
| C83 | 4-Cl—Ph | 3-Py | 2-F, 4-Cl—Ph | H | H | |
| C84 | 2,4-F₂—Ph | 3-Py | 4-Cl—Ph | H | Me | 190-194° C. |
| C85 | 4-Cl—Ph | 3-Py | 4-F—Ph | H | Me | 394/396 |
| C86 | 3-F—Ph | 3-Py | 4-Cl—Ph | H | Me | 394/396 |
| C87 | 2-F—Ph | 3-Py | 4-Cl—Ph | H | Me | 394/396 |

In the above table, the following is meant by each abbreviation given for R¹ to R⁵:

| | | | |
|---|---|---|---|
| H | Hydrogen | 4-Br—Ph | (4-bromophenyl structure) |
| Me | (methyl structure) | 2-Fl—Ph | (2-fluorophenyl structure) |
| Et | (ethyl structure) | 2-Cl—Ph | (2-chlorophenyl structure) |

-continued
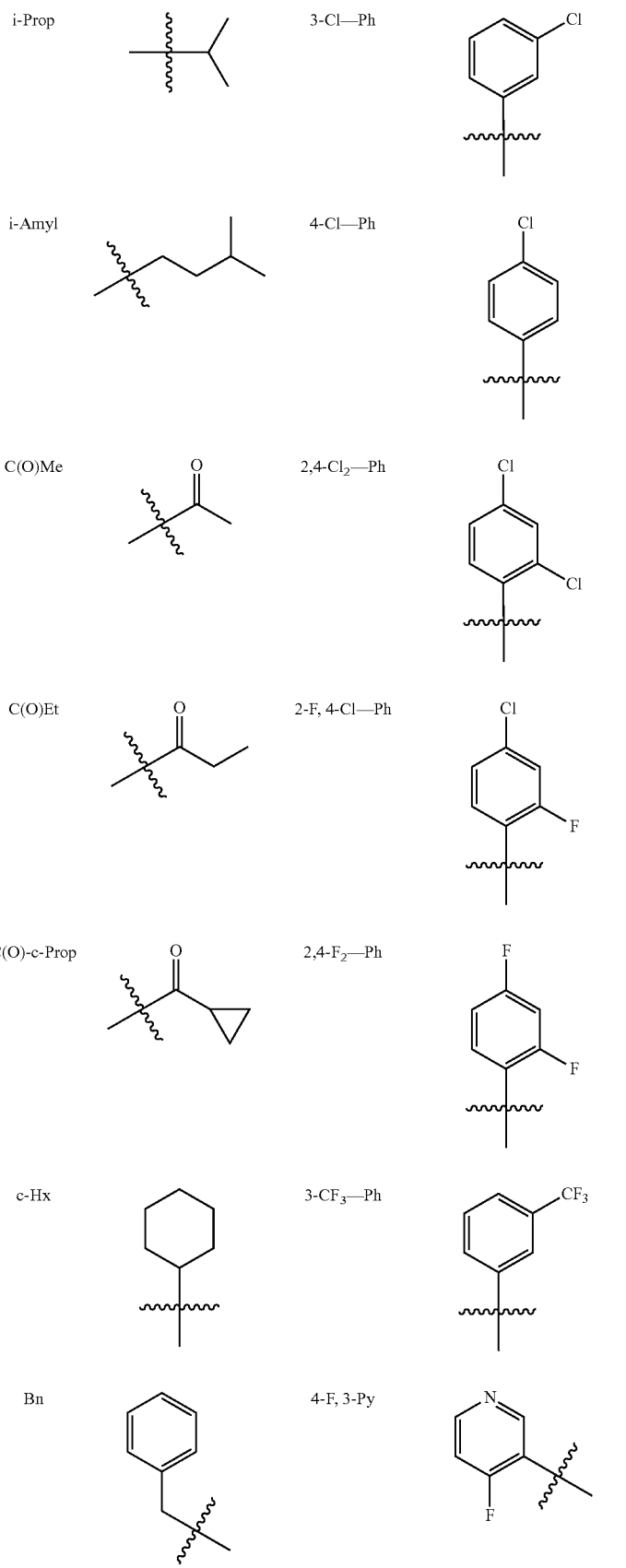

-continued

| | | | |
|---|---|---|---|
| Ph | 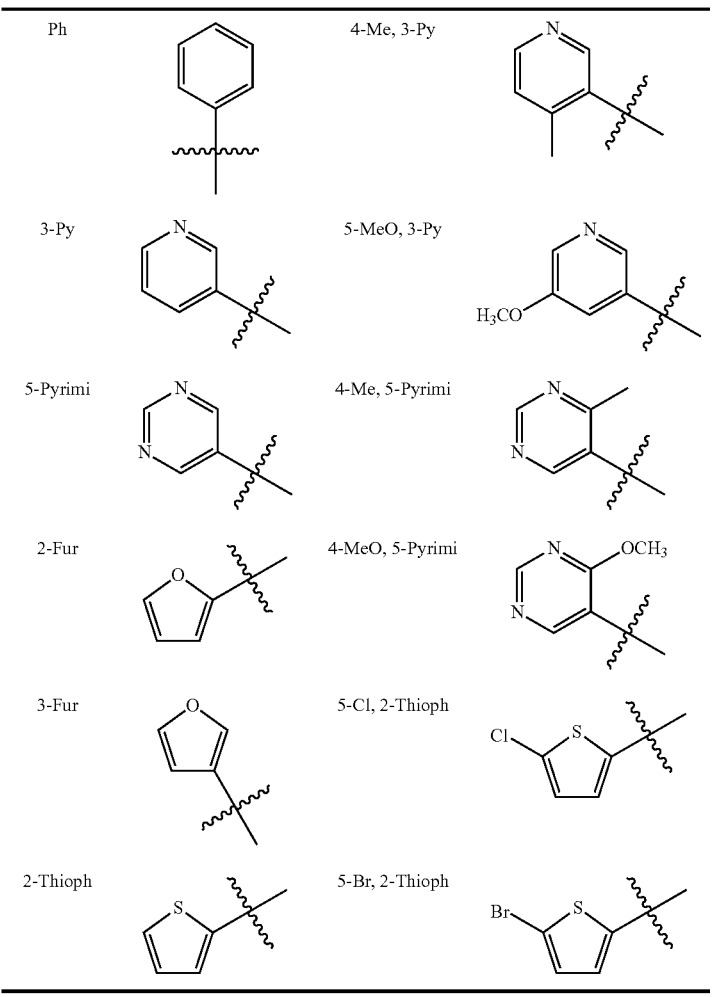 | 4-Me, 3-Py | |
| 3-Py | | 5-MeO, 3-Py | |
| 5-Pyrimi | | 4-Me, 5-Pyrimi | |
| 2-Fur | | 4-MeO, 5-Pyrimi | |
| 3-Fur | | 5-Cl, 2-Thioph | |
| 2-Thioph | | 5-Br, 2-Thioph | |

Compounds of the invention and for use in the methods of the invention can be made, for example, by following the reaction schemes and the methods detailed below. The starting materials used for the preparation of the compounds of the invention may be purchased from usual commercial suppliers or may be prepared by known methods. The starting materials as well as the intermediates may be purified before use in the next step by state of the art methodologies such as chromatography, crystallization, distillation and filtration.

Preparation of Compounds of Formula Ia

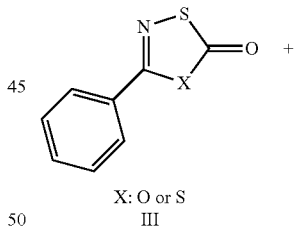

X: O or S
III

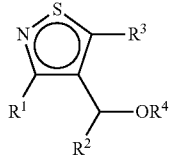

Ia

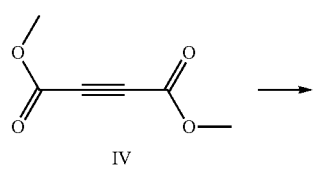

IV

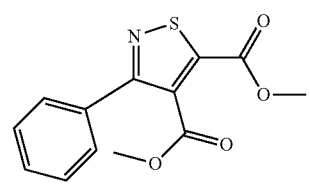

V

Methods for the preparation of isothiazoles are reviewed in Science of Synthesis (2002), 11, 507-572.

3-Substituted isothiazoles can be prepared by 1,3-dipolar cycloaddition, as described in Synthetic Communications, 35(6), 807, 2005 or ARKIVOC (3), 121, 2002.

Compounds of type V are converted to final products as described in the Examples.

Other useful intermediates for the preparation of compounds of type Ia are found in the following journals:

Chemistry Letters; 1984, 1691-92:

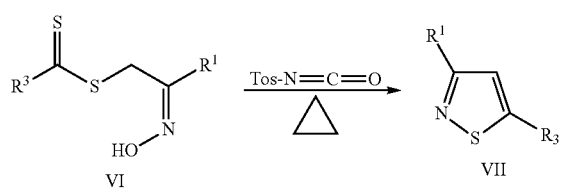

Journal of Heterocyclic Chemistry; 1989, 1575:

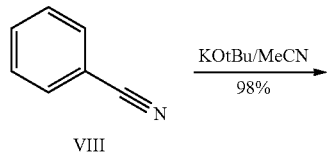

Pd-catalyzed cross coupling reactions can be used to convert 3,5-dihalo-isothiazole-4-carbonitriles XII into final compounds of formula Ia. Experimental details for such transformations can be found in Perk I, 2006, 3681:

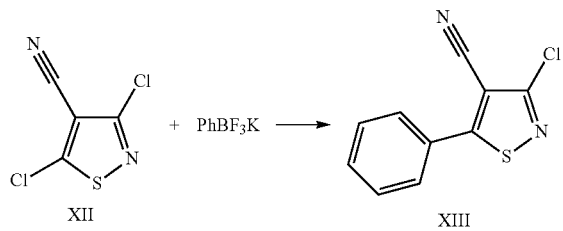

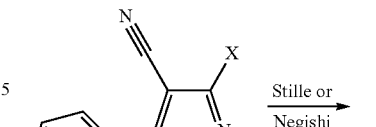

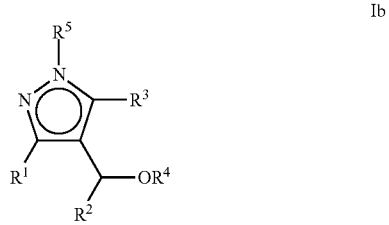

Preparation of Compounds of Formula Ib and Ic

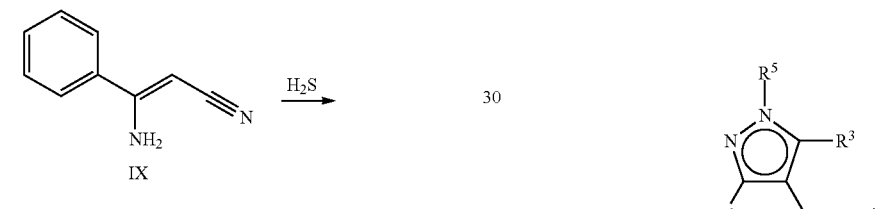

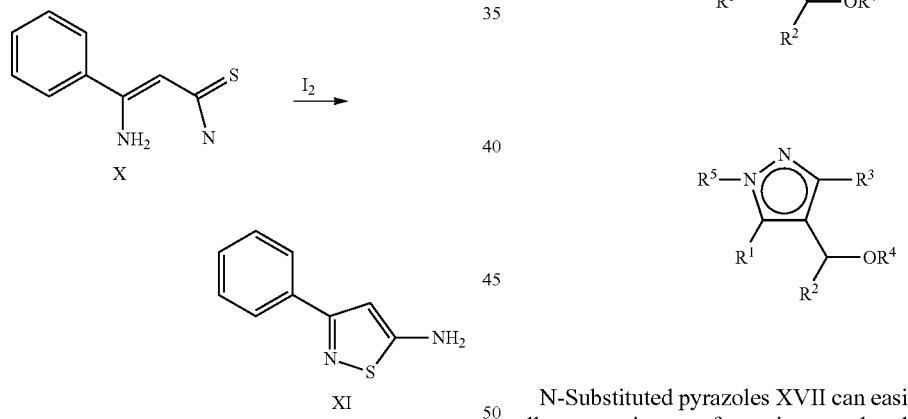

N-Substituted pyrazoles XVII can easily be prepared usually as a mixture of two isomers by the reaction of 1,3-diketones (XVI) with hydrazine or hydrazine derivatives. (Advances in Heterocyclic Chemistry; 1966, 6, 347):

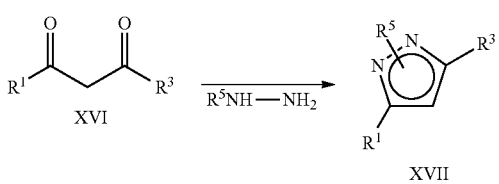

Alternatively 1,3-diketones could be prepared directly from ketones (XVIII) and acid chlorides (XIX) and then convert them in situ into pyrazoles by addition of hydrazine or hydrazine derivatives (Organic Letters 2006, 8, 13, 2675):

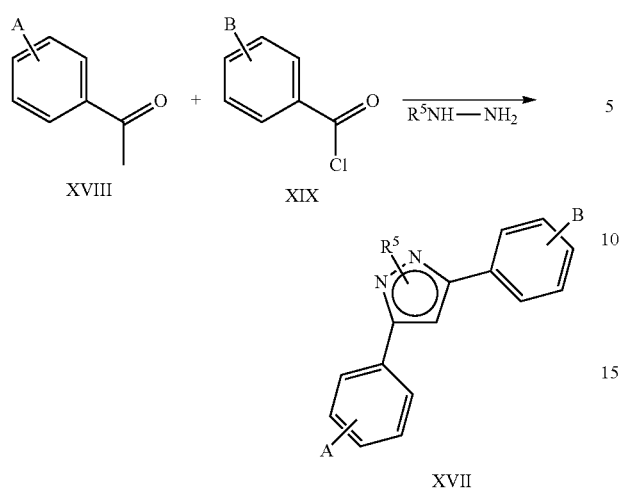

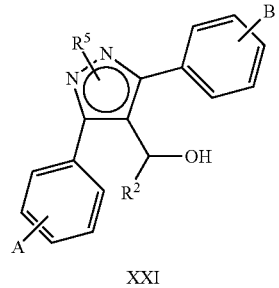

wherein A and B are any substituent in any position of the aryl ring.

Bromination of the intermediate XVII at C4 can be performed using conditions as described in Journal of Heterocyclic Chemistry 2006, 43, 1669:

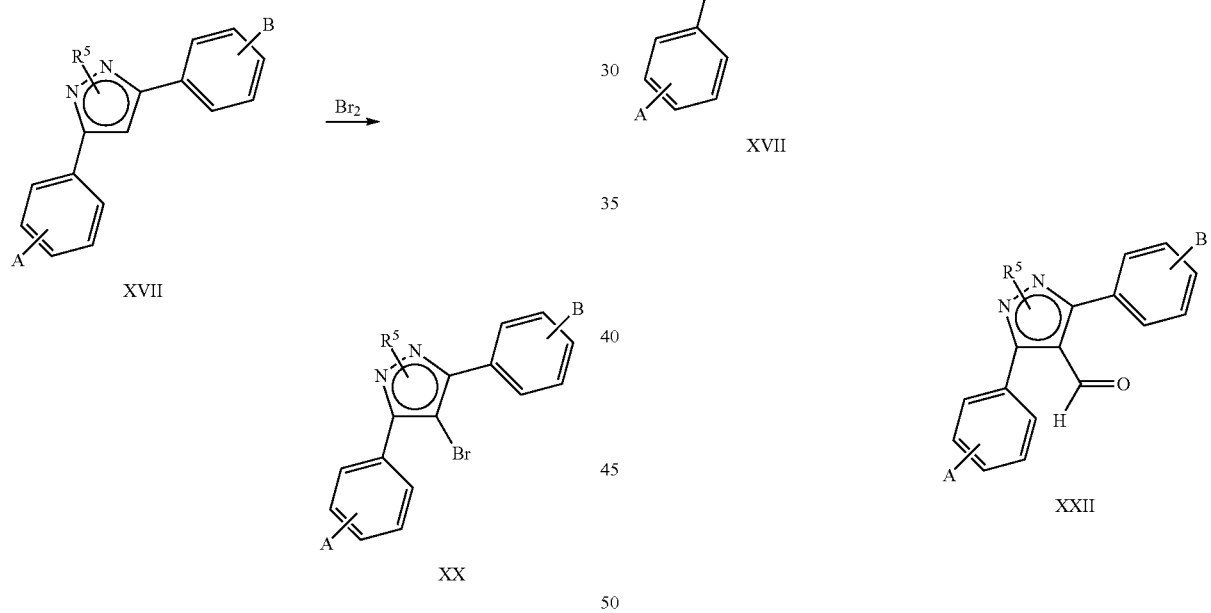

Metallation of the intermediate XX in position 4 followed by trapping with an aldehyde will lead to compounds of type XXI (Archiv der Pharmazie 1987, 320, 12, 1267):

Alternatively Vilsmeier-Haack formylation on XVII will afford directly 4-formyl derivates XXII (Journal of Medicinal Chemistry; 2003, 46, 1144):

Intermediate XXII can further react with a Grignard or lithiated species to afford final compounds XXI:

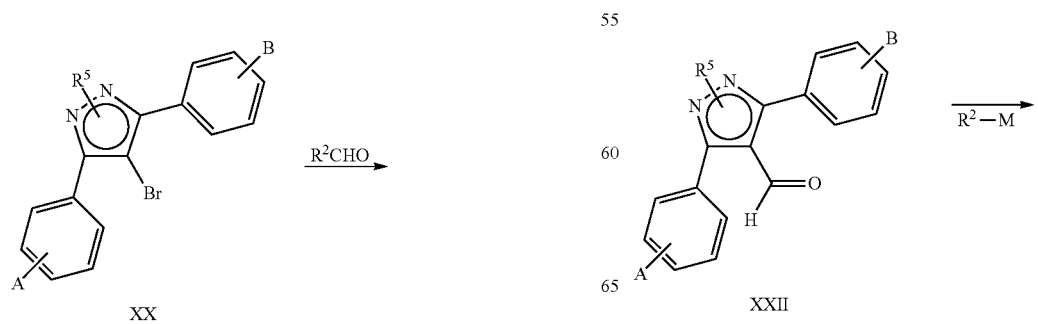

-continued

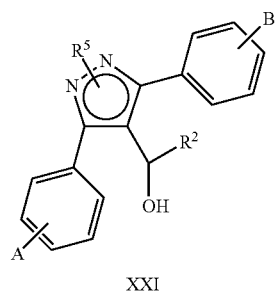

XXI

Tetrahedron 2004, 60, 901:

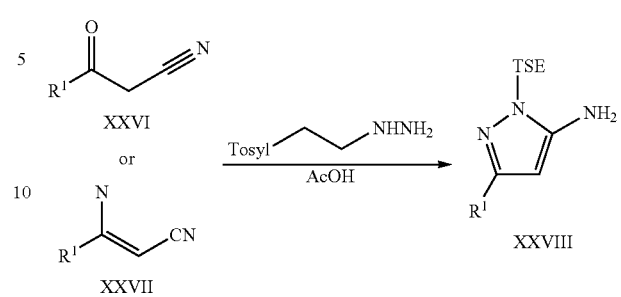

Other useful intermediates for the preparation of compounds of type Ib or Ic are found in the following journals and patent applications:

Chemische Berichte, 1968, 101, 536:

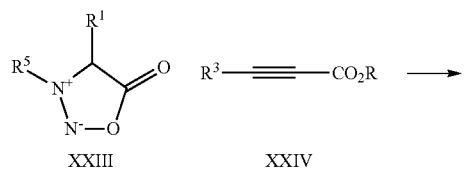

XXIII    XXIV

PCT Publication number WO 2006/092510:

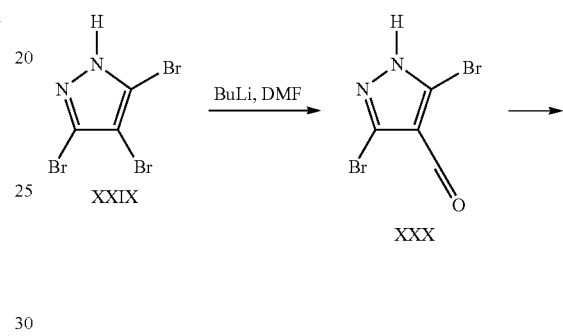

XXIX

XXX

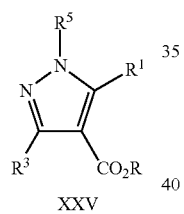

XXV

XXXI wherein PG is a protecting group.

wherein R is an optionally substituted alkyl group.

Synlett 2004, 5, 795 and reference cited therein:

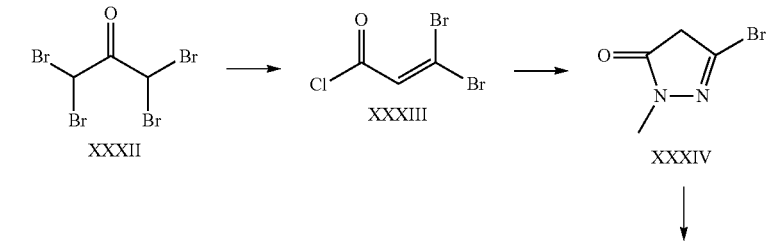

XXXII    XXXIII    XXXIV

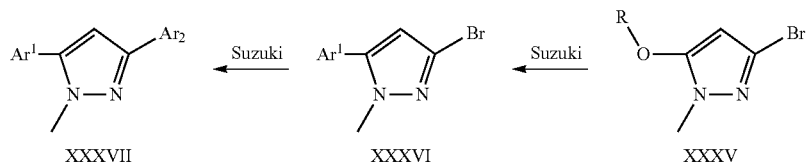

XXXVII    XXXVI    XXXV wherein R is $CF_3SO_2$ or $C_4F_4SO_2$ and $Ar^1$ and $Ar^2$ are optionally substituted aryl groups.

A review about the synthesis of pyrazoles can be found in Advances in Heterocyclic Chemistry 1990, 48, 223-99.

The compounds of the present invention are useful in controlling plant pathogenic fungi when they are applied to a plant or plant propagation material or the locus thereof in a fungicidally effective amount. Accordingly, therefore, the present invention also provides a method of preventing and/or controlling fungal infection in plants and/or plant propagation material comprising applying to the plant or plant propagation material or the locus thereof a fungicidally effective amount of a compound of formula I.

By 'plant propagation material' is meant generative parts of a plant including seeds of all kinds (fruit, tubers, bulbs, grains etc), roots, rhizomes, cuttings, cut shoots and the like. Plant propagation material may also include plants and young plants which are to be transplanted after germination or after emergence from the soil.

By "locus" is meant the fields on which the plants to be treated are growing, or where the seeds of cultivated plants are sown, or the place where the seed will be placed into the soil.

The compounds of the present invention may be used against phytopathogenic fungi of the following classes: Fungi imperfecti (e.g. *Botrytis*, *Pyricularia*, *Helminthosporium*, *Fusarium*, *Septoria*, *Cercospora* and *Alternaria*), Basidiomycetes (e.g. *Rhizoctonia*, *Hemileia*, *Puccinia*), Ascomycetes (e.g. *Venturia* and *Erysiphe*, *Podosphaera*, *Monilinia*, *Uncinula* and *Pyrenophora*) and Oomycetes (e.g. *Phytophthora*, *Pythium*, *Plasmopara*). In particular, the compounds of the present invention may be used against *Helminthosporium* spp., *Fusarium* spp., *Septoria* spp., *Cercospora* spp., *Alternaria* spp., *Rhizoctonia* spp., *Puccinia* spp., *Venturia* spp., *Erysiphe* spp., *Podosphaera* spp., *Monilinia* spp., *Uncinula* spp. and *Pyrenophora* spp.

The compounds of the present invention are suitable for controlling fungal disease on a number of plants and their propagation material including, but not limited to the following target crops: cereals (wheat, barley, rye, oats, maize (including field corn, pop corn and sweet corn), rice, sorghum and related crops); beet (sugar beet and fodder beet); leguminous plants (beans, lentils, peas, soybeans); oil plants (rape, mustard, sunflowers); cucumber plants (marrows, cucumbers, melons); fibre plants (cotton, flax, hemp, jute); vegetables (spinach, lettuce, asparagus, cabbages, carrots, eggplants, onions, pepper, tomatoes, potatoes, paprika, okra); plantation crops (bananas, fruit trees, rubber trees, tree nurseries), ornamentals (flowers, shrubs, broad-leaved trees and evergreens, such as conifers); as well as other plants such as vines, bushberries (such as blueberries), caneberries, cranberries, peppermint, rhubarb, spearmint, sugar cane and turf grasses including, but not limited to, cool-season turf grasses (for example, bluegrasses (*Poa* L.), such as Kentucky bluegrass (*Poa pratensis* L.), rough bluegrass (*Poa trivialis* L.), Canada bluegrass (*Poa compressa* L.) and annual bluegrass (*Poa annua* L.); bentgrasses (*Agrostis* L.), such as creeping bentgrass (*Agrostis palustris* Huds.), colonial bentgrass (*Agrostis tenius* Sibth.), velvet bentgrass (*Agrostis canina* L.) and redtop (*Agrostis alba* L.); fescues (*Festuca* L.), such as tall fescue (*Festuca arundinacea* Schreb.), meadow fescue (*Festuca elatior* L.) and fine fescues such as creeping red fescue (*Festuca rubra* L.), chewings fescue (*Festuca rubra* var. *commutata* Gaud.), sheep fescue (*Festuca ovina* L.) and hard fescue (*Festuca longifolia*); and ryegrasses (*Lolium* L.), such as perennial ryegrass (*Lolium perenne* L.) and annual (Italian) ryegrass (*Lolium multiflorum* Lam.)) and warm-season turf grasses (for example, Bermudagrasses (*Cynodon* L. C. Rich), including hybrid and common Bermudagrass; Zoysiagrasses (*Zoysia Willd.*), St. Augustinegrass (*Stenotaphrum secundatum* (Walt.) Kuntze); and centipedegrass (*Eremochloa ophiuroides* (Munro.) Hack.)).

In addition 'crops' are to be understood to include those crops that have been made tolerant to pests and pesticides, including herbicides or classes of herbicides, as a result of conventional methods of breeding or genetic engineering. Tolerance to e.g. herbicides means a reduced susceptibility to damage caused by a particular herbicide compared to conventional crop breeds. Crops can be modified or bred so as to be tolerant, for example, to HPPD inhibitors such as mesotrione or EPSPS inhibitors such as glyphosate.

The compounds of formula I may be in unmodified form or, preferably, may be incorporated into fungicidal compositions. Typically the compounds of formula I are therefore formulated together with carriers and adjuvants conventionally employed in the art of formulation, using methods well known to the person skilled in the field of formulation.

The invention therefore also relates to a composition for the control of fungal infection comprising a compound of formula I and an agriculturally acceptable carrier or diluent.

The invention also relates to a composition for the control of fungal infection comprising a compound of formula I and an agriculturally acceptable carrier or diluent that further comprises at least one additional fungicide.

The agrochemical composition will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Suitably, the agrochemical compositions of the present invention are applied prior to disease development. Rates and frequency of use of the formulations are those conventionally used in the art and will depend on the risk of infestation by the fungal pathogen, the developmental stage of the plant and on the location, timing and application method. Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds.

In practice, as indicated above, the agrochemical compositions comprising compound of formula I are applied as a formulation containing the various adjuvants and carriers known to or used in the industry. They may thus be formulated as granules, as wettable or soluble powders, as emulsifiable concentrates, as coatable pastes, as dusts, as flowables, as solutions, as suspensions or emulsions, or as controlled release forms such as microcapsules. These formulations are described in more detail below and may contain as little as about 0.5% to as much as about 95% or more by weight of the active ingredient. The optimum amount will depend on formulation, application equipment and nature of the plant pathogenic fungi to be controlled.

Suspension concentrates are aqueous formulations in which finely divided solid particles of the active compound are suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from about 0.5% to about 95% of the concentrate.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other nonvolatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles and are usually applied without dilution to the area in which control of plant pathogenic fungi is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre and preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Suitable agricultural adjuvants and carriers that are useful in formulating the compositions of the invention in the formulation types described above are well known to those skilled in the art. Suitable examples of the different classes are found in the non-limiting list below.

Liquid carriers that can be employed include water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc. ethylene glycol, propylene glycol, glycerine, N-methyl-2-pyrrolidinone, and the like. Water is generally the carrier of choice for the dilution of concentrates.

Suitable solid carriers include talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour, lignin and the like.

A broad range of surface-active agents are advantageously employed in both said liquid and solid compositions, especially those designed to be diluted with carrier before application. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, anti-foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants, sticking agents, and the like.

In addition, further, other biocidally active ingredients or compositions may be combined with the compound of formula I and used in the methods of the invention and applied simultaneously or sequentially with the compound of formula I. When applied simultaneously, these further active ingredients may be formulated together with the compound of formula I or mixed in, for example, the spray tank. These further biocidally active ingredients may be fungicides, herbicides, insecticides, bactericides, acaricides, nematicides and/or plant growth regulators. Accordingly, the present invention provides a composition comprising (i) a compound of formula I and a further fungicide, (ii) a compound of formula I and a herbicide, (iii) a compound of formula I and an insecticide, (iv) a compound of formula I and a bactericide; (v) a compound of formula I and an acaricide, (vi) a compound of formula I and a nematicide and/or (vii) a compound of formula I and a plant growth regulator. In addition, the compounds of the invention may also be applied with one or more systemically acquired resistance inducers ("SAR" inducer). SAR inducers are known and described in, for example, U.S. Pat. No. 6,919,298 and include, for example, salicylates and the commercial SAR inducer acibenzolar-5-methyl.

In particular, composition encompassed by the present invention include, but are not limited to, compositions comprising a compound of formula I and acibenzolar (CGA245704), a compound of formula I and ancymidol, a compound of formula I and alanycarb, a compound of formula I and aldimorph, a compound of formula I and amisulbrom, a compound of formula I and anilazine, a compound of formula I and azaconazole, a compound of formula I and azoxystrobin, a compound of formula I and benalaxyl, a compound of formula I and benthiavalicarb, a compound of formula I and benomyl, a compound of formula I and biloxazol, a compound of formula I and bitertanol, a compound of formula I and bixafen, a compound of formula I and blasticidin S, a compound of formula I and boscalid, a compound of formula I and bromuconazole, a compound of formula I and bupirimate, a compound of formula I and captafol, a compound of formula I and captan, a compound of formula I and carbendazim, a compound of formula I and carbendazim, a compound of formula I and chlorhydrate, a compound of formula I and carboxin, a compound of formula I and carpropamid, a compound of formula I and carvone, a compound of formula I and CGA41396, a compound of formula I and CGA41397, a compound of formula I and chinomethionate, a compound of formula I and chloroneb, a compound of formula I and chlorothalonil, a compound of formula I and chlorozolinate, a compound of formula I and clozylacon, a compound of formula I and copper containing compounds such as copper oxychloride, copper oxyquinolate, copper sulphate, copper tallate and Bordeaux mixture, a compound of formula I and cyflufenamid, a compound of formula I and cymoxanil, a compound of formula I and cyproconazole, a compound of formula I and cyprodinil, a compound of formula I and debacarb, a compound of formula I and di-2-pyridyl disulphide 1,1'-dioxide, a compound of formula I and dichlofluanid, a compound of formula I and diclomezine, a compound of formula I and dichlozoline, a compound of formula I and dichlone, a compound of formula I and dicloran, a compound of formula I and diclocymet, a compound of formula I and diethofencarb, a compound of formula I and difenoconazole, a compound of formula I and difenzoquat, a compound of formula I and diflumetorim, a compound of formula I and O,O-di-iso-propyl-5-benzyl thiophosphate, a compound of formula I and dimefluazole, a compound of formula I and dimetconazole, a compound of formula I and dimethomorph, a compound of formula I and dimethirimol, a compound of formula I and dimoxystrobin, a compound of formula I and diniconazole, a compound of formula I and dinocap, a compound of formula I and dithianon, a compound of formula I and dodecyl dimethyl ammonium chloride, a compound of formula I and dodemorph, a compound of formula I and dodine, a compound of formula I and doguadine, a compound of formula I and edifenphos, a compound of formula I and enestrobin, a compound of formula I and epoxiconazole, a compound of formula I and ethaboxam, a compound of formula I and ethirimol, a compound of formula I and etridiazole, a compound of formula I and famoxadone, a compound of formula I and fenamidone (RPA407213), a compound of formula I and fenarimol, a compound of formula I and fenbuconazole, a compound of formula I and fenfuram, a compound of formula I and fenhexamid (KBR2738), a compound of formula I and fenoxanil, a compound of formula I and fenpiclonil, a compound of formula I and fenpropidin, a compound of formula I and fenpropimorph, a compound of formula I and fentin acetate, a compound of formula I and fentin hydroxide, a compound of formula I and ferbam, a compound of formula I and ferimzone, a compound of formula I and fluazinam, a compound of formula I and fluopicolide, a compound of formula I and fludioxonil, a compound of formula I and fluoxastrobin, a compound of formula I and flumetover, a compound of formula I and SYP-LI90 (flumorph), a compound of formula I and fluopyram, a compound of formula I and fluoroimide, a compound of formula I and fluquinconazole, a compound of formula I and flusilazole, a compound of formula I and flusulfamide, a compound of formula I and flutolanil, a compound of formula I and flutriafol, a compound of formula I and folpet, a compound of formula I and fosetyl-aluminum, a compound of formula I and fuberidazole, a compound of formula I and furalaxyl, a compound of formula I and furametpyr, a compound of formula I and guazatine, a compound of formula I and hexaconazole, a compound of formula I and hydroxyisoxazole, a compound of formula I and hymexazole, a compound of formula I and IKF-916 (cyazofamid), a compound of formula I and imazalil, a compound of formula I and imibenconazole, a compound of formula I and iminoctadine, a compound of formula I and iminoctadine triacetate, a compound of formula I and ipconazole, a compound of formula I and iprobenfos, a compound of formula I and iprodione, a compound of formula I and iprovalicarb (SZX0722), a compound of formula I and isopropanyl butyl carbamate, a compound of formula I and isoprothiolane, a compound of formula I and kasugamycin, a compound of formula I and kresoxim-methyl, a compound of formula I and LY186054, a compound of formula I and LY211795, a compound of formula I and LY248908, a compound of formula I and maneb, a compound of formula I and mancopper, a compound of formula I and mancozeb, a compound of formula I and mandipropamid, a compound of formula I and mefenoxam, a compound of formula I and mepanipyrim, a compound of formula I and mepronil, a compound of formula I and metalaxyl, a compound of formula I and metconazole, a compound of formula I and methasulfocarb, a compound of formula I and metiram, a compound of formula I and metiram-zinc, a compound of formula I and metominostrobin, a compound of formula I and metrafenone, a compound of formula I and myclobutanil, a compound of formula I and myclozoline, a compound of formula I and neoasozin, a compound of formula I and nickel dimethyldithiocarbamate, a compound of formula I and nitrothal-isopropyl, a compound of formula I and nuarimol, a compound of formula I and ofurace, a compound of formula I and organomercury compounds, a compound of formula I and orysastrobin, a compound of formula I and oxadixyl, a compound of formula I and oxasulfuron, a compound of formula I and oxine-copper, a compound of formula I and oxolinic acid, a compound of formula I and oxpoconazole, a compound of formula I and oxycarboxin, a compound of formula I and pefurazoate, a compound of formula I and penconazole, a compound of formula I and pencycuron, a compound of formula I and penthiopyrad, a compound of formula I and phenazin oxide, a compound of formula I and phosdiphen, a compound of formula I and phosphorus acids, a compound of formula I and phthalide, a compound of formula I and picoxystrobin (ZA1963), a compound of formula I and polyoxin D, a compound of formula I and polyram, a compound of formula I and probenazole, a compound of formula I and prochloraz, a compound of formula I and procymidone, a compound of formula I and propamocarb, a compound of formula I and propiconazole, a compound of formula I and propineb, a compound of formula I and propionic acid, a compound of formula I and proquinazid, a compound of formula I and prothioconazole, a compound of formula I and pyraclostrobin, a compound of formula I and pyrazophos, a compound of formula I and pyribencarb, a compound of formula I and pyrifenox, a compound of formula I and pyrimethanil, a compound of formula I and pyroquilon, a compound of formula I and pyroxyfur, a compound of formula I and pyrrolnitrin, a compound of formula I and quaternary ammonium compounds, a compound of formula I and quinomethionate, a compound of formula I and quinoxyfen, a compound of formula I and quintozene, a compound of formula I and silthiofam, a compound of formula I and simeconazole, a compound of formula I and sipconazole (F-155), a compound of formula I and sodium pentachlorophenate, a compound of formula I and spiroxamine, a compound of formula I and streptomycin, a compound of formula I and sulphur, a compound of formula I and tebuconazole, a compound of formula I and tecloftalam, a compound of formula I and tecnazene, a compound of formula I and tetraconazole, a compound of formula I and thiabendazole, a compound of formula I and thifluzamid, a compound of formula I and 2-(thiocyanomethylthio)benzothiazole, a compound of formula I and thiophanate-methyl, a compound of formula I and thiram, a compound of formula I and tiadinil, a compound of formula I and timibenconazole, a compound of formula I and tolclofos-methyl, a compound of formula I and tolylfluanid, a compound of formula I and triadimefon, a compound of formula I and triadimenol, a compound of formula I and triazbutil, a compound of formula I and triazoxide, a compound of formula I and tricyclazole, a compound of formula I and tridemorph, a compound of formula I and trifloxystrobin (CGA279202), a compound of formula I and triforine, a compound of formula I and triflumizole, a compound of formula I and triticonazole, a compound of formula I and validamycin A, a compound of formula I and vapam, a compound of formula I and valiphenal a compound of formula I and vinclozolin, a compound of formula I and zineb, a compound of formula I and ziram, a compound of formula I and zoxamide, a compound of formula I and 3-[5-(4-chlorophenyl)-2,3-dimethylisoxazolidin-3-yl]pyridine, a compound of formula I and 5-chloro-7-(4-methylpiperidine-1-yl)-6-(2,4,6-trifluorophenyl)[1,2,4]triazolo[1,5-a]pyrimidine and a compound of formula I and N-(4-chloro-2-nitrophenyl)-N-ethyl-4-methyl-benzsulfonamide.

The formulations of the invention and for use in the methods of the invention can be applied to the areas where control is desired by conventional methods such as spraying, atomising, dusting, scattering, coating or pouring. Dust and liquid compositions, for example, can be applied by the use of power-dusters, broom and hand sprayers and spray dusters. The formulations can also be applied from airplanes as a dust or a spray or by rope wick applications. A preferred method of applying the formulation of the invention is foliar application. In addition, both solid and liquid formulations may also be applied to the soil in the locus of the plant to be treated allowing the active ingredient to penetrate the plant through the roots. The formulations of the invention may also be used for dressing applications on plant propagation material to provide protection against fungus infections on the plant propagation material as well as against phytopathogenic fungi occurring in the soil. Suitably, the active ingredient may be applied to plant propagation material to be protected by impregnating the plant propagation material, in particular, seeds, either with a liquid formulation of the fungicide or coating it with a solid formulation. In special cases, other types of application are also possible, for example, the specific treatment of plant cuttings or twigs serving propagation. It is noted that, whereas it is preferred to formulate commercial products as concentrates, the end user will normally use dilute formulations.

Furthermore, the compounds of formula I find general use as fungicides and may therefore also be used in methods to control pathogenic fungi in related areas, for example in the protection of technical materials, in food storage or in hygiene management. As such, the present invention further provides the use of a compound of formula I for preventing and/or controlling fungal infection on technical materials, in food storage or in hygiene management. In addition, the present invention also provides a method for controlling and/or preventing infestation of technical materials by fungi comprising applying the compound of formula Ito the technical material or the locus thereof in a fungicidally effective amount.

"Technical materials" include but are not limited to organic and inorganic materials such as wood, paper, leather, natural and synthetic fibers, composites thereof such as particle board, plywood, wall-board and the like, woven and non-woven fabrics, construction surfaces and materials (e.g. building material), cooling and heating system surfaces and materials, ventilation and air conditioning system surfaces and materials, and the like. The compounds and combinations according the present invention can be applied to such materials or surfaces in an amount effective to inhibit or prevent disadvantageous effects such as decay, discoloration or mold in like manner as described above. Structures and dwellings constructed using or incorporating technical materials in which such compounds or combinations have been applied are likewise protected against attack by fungi.

The technical material can be treated with a compound of formula I in a number of ways, including, but not limited to, by including the compound in the technical material itself, absorbing, impregnating, treating (in closed pressure or vacuum systems) said material with said compound, dipping or soaking the building material, or coating the material for example by curtain coating, roller, brush, spray, atomisation, dusting, scattering or pouring application. The compound of the invention can be formulated for use in treatment of technical materials by using techniques well known to the person skilled in the art. Such formulations may utilise, for example, the formulation materials listed above in relation to agrochemical formulations.

In addition to the foregoing, active compounds of the present invention can be used in the treatment of fungal infections of human and animal subjects (including but not limited to horses, cattle, sheep, dogs, cats, etc.) for medical and veterinary purposes. When the compounds of the present invention are administered as pharmaceuticals, to humans and animals, they can be given per se or, more typically as a pharmaceutical composition.

Accordingly, the present invention therefore provides a composition comprising a compound of formula I and a pharmaceutically acceptable carrier or diluent. In addition, the present invention also provides a method of treating fungal infection in a subject in need thereof, comprising administering a compound of formula Ito said subject in an amount effective to treat said fungal infection. Furthermore, the present invention provides the use of a compound of formula I as a pharmaceutical and in a method for the manufacture of a medicament for the treatment of fungal infection.

Examples of such infections include but are not limited to ailments such as Onychomycosis, sporotichosis, hoof rot, jungle rot, *Pseudallescheria boydii*, scopulariopsis or athletes foot, sometimes generally referred to as "white-line" disease, as well as fungal infections in immunocompromised patients such as AIDS patients and transplant patients. Thus, fungal infections may be of skin or of keratinaceous material such as hair, hooves, or nails, as well as systemic infections such as those caused by *Candida* spp., *Cryptococcus neoformans*, and *Aspergillus* spp., such as in pulmonary aspergillosis and *Pneumocystis carinii* pneumonia.

"Pharmaceutically acceptable" means compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically-acceptable carrier" as used herein means a pharmaceutically-acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Compositions of the present invention for pharmaceutical use include those suitable for oral, nasal, topical (including buccal and sublingual), rectal, vaginal and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration but will generally be that amount of the active ingredient which produces a therapeutic effect. Generally, this amount will range from about 1% to about 99% of active ingredient, preferably from about 5% to about 70%, most preferably from about 10% to about 30%.

Pharmaceutical compositions of the invention for topical, nasal, rectal and vaginal use are generally in the form of ointments, pastes, creams, gels powders and sprays. Ointments, pastes, creams and gels may contain, in addition to the compound of formula I, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of formula I, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

In the addition, the pharmaceutical compositions of the invention may also be suitable for oral administration. As such, they may be presented in discrete units, such as capsules, cachets, lozenges, or tablets, each containing a predetermined amount of the compound of formula I; as a powder or granules; as a solution or a suspension in an aqueous or non-aqueous liquid; or as an oil-in-water or water-in-oil emulsion.

Pharmaceutical compositions of this invention suitable for parenteral administration comprise a compound of formula I in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of the action of microorganisms may be ensured by the inclusion of various antibacterial and other antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The pharmaceutical compositions of the present invention may be given by any suitable means of administration including orally, parenterally, topically, transdermally, rectally, etc. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Topical or parenteral administration is preferred.

"Parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

Actual dosage levels of the active ingredients in the pharmaceutical compositions of this invention may be varied so as to obtain an amount of the active ingredient which is effective to achieve the desired therapeutic response, e.g., antimycotic activity, for a particular patient, composition, and mode of administration, without being toxic to the patient. The selected dosage level will depend upon a variety of factors including the activity of the particular active compound employed, the route of administration, the time of administration, the rate of excretion of the particular active compound being employed, the duration of the treatment, other drugs, compounds and/or materials used in combination with the particular inhibitor employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. As a general proposition, a dosage from about 0.01 or 0.1 to about 50, 100 or 200 mg/kg will have therapeutic efficacy, with all weights being calculated based upon the weight of the active compound, including the cases where a salt is employed.

The present invention will now be described by way of the following non-limiting examples. Those skilled in the art will promptly recognize appropriate variations from the procedures both as to reactants and as to reaction conditions and techniques.

EXAMPLES

Example 1

Preparation of [3-(4-Chloro-phenyl)-5-phenyl-isothiazol-4-yl]-pyridin-3-yl-methanol (compound A1; see Table I)

Step a: 5-(4-Chloro-phenyl)-[1,3,4]oxathiazol-2-one (3)

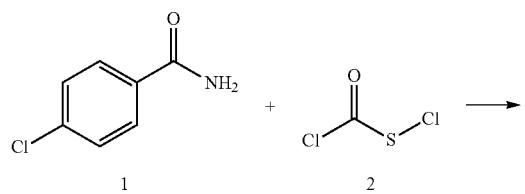

-continued

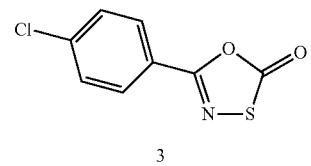

3

To a suspension of 1 (778 mg) in 10 ml of toluene is added 0.85 ml of chlorocarbonylsulfenyl chloride and the mixture is heated at 100° C. for 2 h. Gas evolution is observed and a clear solution is obtained. TLC shows complete conversion. The reaction mixture is concentrated and the solid residue is triturated with pentane, filtered and dried. Yield: 886 mg (82%) of 3 as a white crystalline solid.

Step b:
3-(4-Chloro-phenyl)-isothiazole-4,5-dicarboxylic acid dimethyl ester (5)

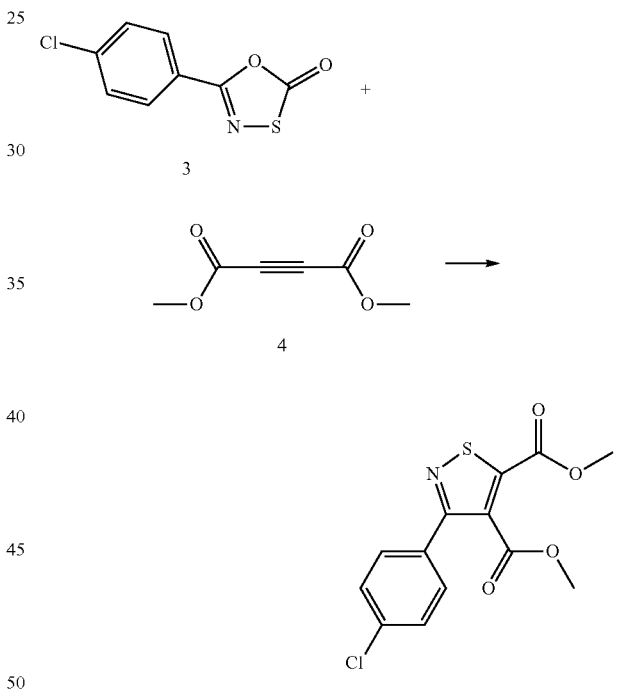

To a solution of 3 (1.068 g) in 10 ml of α,α,α-trifluorotoluene is added 2.0 ml of dimethyl acetylenedicarboxylate and the mixture is heated in the microwave at 170° C. for 1 h. GCMS shows complete conversion into product 5.

The reaction mixture is concentrated and the oily residue (containing excess 4) is purified by flash column chromatography (20% EtOAc in heptane). The fractions containing product are combined and concentrated. Reactant 4 is still present. It is successfully removed by addition of pentane and taking of the solvent with a pipette. This process is repeated four times. Compound 5 is obtained as a white solid with a melting point: 106.5-107.5° C.

Step c:
3-(4-Chloro-phenyl)-isothiazole-4,5-dicarboxylic acid (6)

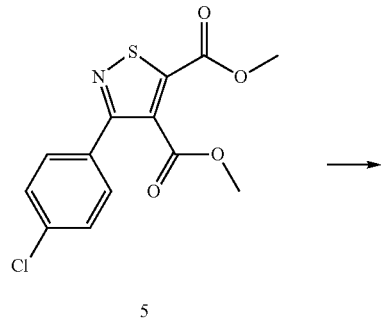

5

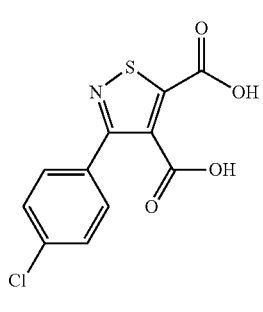

6

A solution of 4.4 g of 5 and 2.8 g of NaOH in 20 ml of water is kept at reflux for 2.5 h. The reaction mixture is cooled, diluted with water (150 ml) and acidified with conc. HCl (aq). A precipitate forms. The water layer is extracted with EtOAc (2×200 ml; the precipitate slowly dissolves). The combined organic layers are washed with brine and dried (Na₂SO₄). Concentration afforded 3.9 grams of 6 as a white solid.

Step d: 3-(4-Chloro-phenyl)-isothiazole-4-carboxylic acid (7)

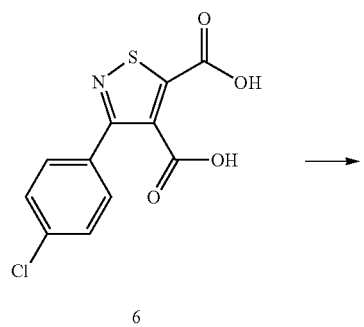

6

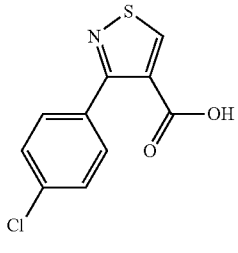

7

A suspension of 6 (3.9) g in 40 ml of 1,2-dichlorobenzene is held at reflux for 20 min (gas formation is observed). The reaction mixture is cooled (precipitation of product), diluted with pentane (50 ml) and filtered. The cream colored solid is washed with pentane (5×) and dried. This product is still contaminated with 1,2-dichlorobenzene. The crude product is suspended in water (80 ml) and 20 ml 1N NaOH is added, a clear solution results. The water layer is extracted with ether (2×100 ml). The clear water layer is acidified with conc. HCl until pH 2 to 3 (precipitation of product). The product is extracted with EtOAc (2×100 ml). The combined organic layers are washed with brine, dried (Na₂SO₄) and concentrated. Yield: 3.1 g of 7 as an off white solid (melting point: 179.5-180.5° C.).

Step e: 3-(4-Chloro-phenyl)-isothiazole-4-carboxylic acid tert-butyl ester (8)

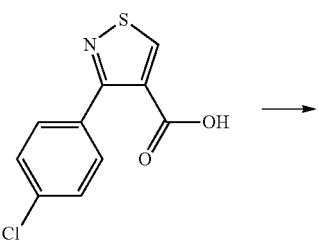

7

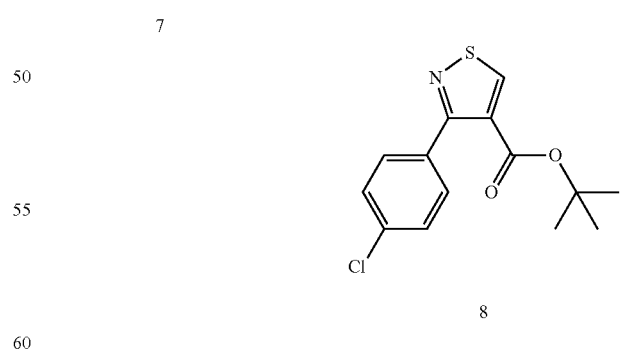

8

To a mixture of 7 (3.35 g), DMAP (1.7 g) and tBuOH (5.2 g) in CH₂Cl₂ (50 ml) is added 3.2 g of EDCI and the clear solution is stirred over the weekend. Additional CH₂Cl₂ (100 ml) is added and the mixture is washed with 1N HCl (2×150 ml), sat. NaHCO₃ (150 ml), brine (150 ml), dried and concentrated. This afforded 3.75 g of 8 as a pale yellow oil.

Step f: 5-Bromo-3-(4-chloro-phenyl)-isothiazole-4-carboxylic acid tert-butyl ester (9)

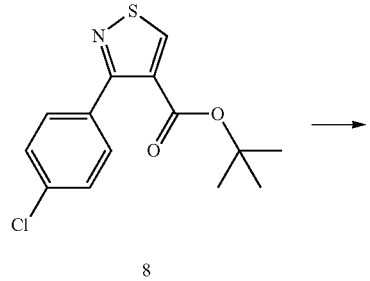

8

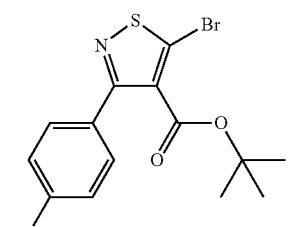

9

A solution of 8 (3.50 g) in THF (60 ml) is cooled to −78° C. under N₂ followed by drop wise addition of BuLi (8.0 ml, 1.6M in hexane). After complete addition stirring is continued at −78° C. for 15 min. Bromine (1.2 ml) is now added drop wise and stirring is continued at −78° C. for 15 min, after which the cooling bath is removed. The mixture is allowed to warm to room temp. TLC shows a good conversion into a slightly faster moving spot (Hep/EA, 9/1). 1N HCl (50 ml) is added and the THF is removed in vacuo. Water (100 ml), containing some sodium thiosulfate, is added and the product is extracted with EtOAc (150 ml). The organic layer is washed with sat. NaHCO₃, brine, dried and concentrated. The orange/red oily residue is purified by flash column chromatography (~50 g silica, 5% diisopropyl ether in heptane) yielding 3.1 g of 9 as a pale yellow oil.

Step g: 3-(4-Chloro-phenyl)-5-phenyl-isothiazole-4-carboxylic acid tert-butylester (11)

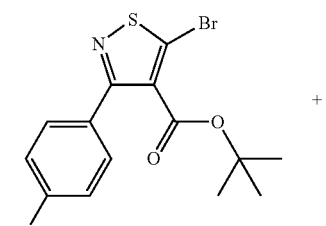

9

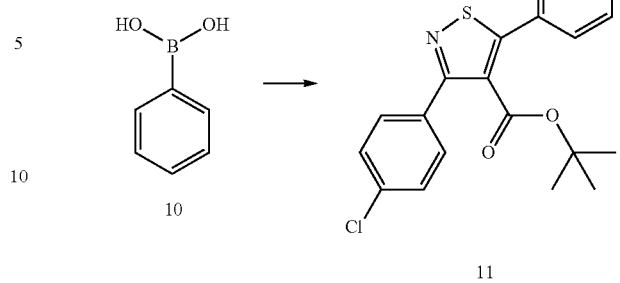

11

Starting material 9 (1.12 g) is dissolved in DME (12 ml) and to this are added 439 mg of 10, water (5 ml) and 954 mg of Na₂CO₃. The mixture is degassed with argon for 5 min. Pd(dppf)Cl₂ (121 mg) is added, the tube is sealed and the reaction mixture is heated at 100° C. in the microwave for 15 min. TLC (Hep/EtOAc, 80/20) shows a good conversion into a slower moving spot. The reaction mixture is diluted with EtOAc and washed with water and brine. The organic layer is dried and concentrated. The residue is purified by flash column chromatography using 5% diisopropyl ether in heptane as eluent. Isothiazole 11 is obtained in good yield as a white crystalline solid.

Step h: 3-(4-Chloro-phenyl)-5-phenyl-isothiazole-4-carboxylic acid (12)

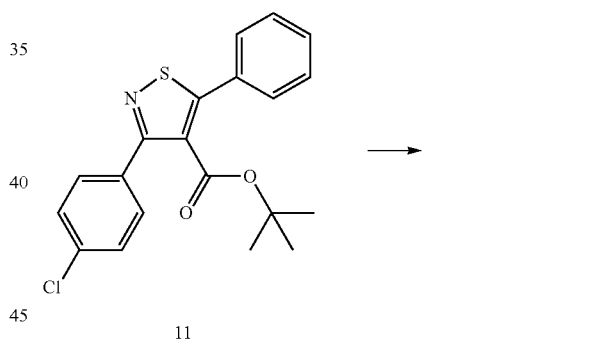

To a solution of 11 (2.35 g) in CH₂Cl₂ (25 ml) is added 25 ml of TFA and the mixture is stirred at room temperature for 24 h. The mixture is then concentrated and the residue is dissolved in ether (250 ml). Water (225 ml) is added followed by 1N NaOH (25 ml). After washing and separation, the basic water layer is extracted once more with ether. The water layer is acidified with conc. HCl and the precipitated product is extracted with ether (2×150 ml). The combined organic layers are washed with brine, dried and concentrated. 1.85 g of 12 is obtained as a cream colored solid.

Step i: 3-(4-Chloro-phenyl)-5-phenyl-isothiazole-4-carboxylic acid methoxy-methyl-amide (14)

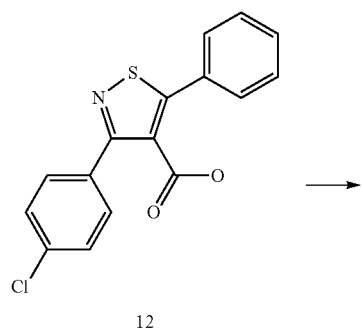

12

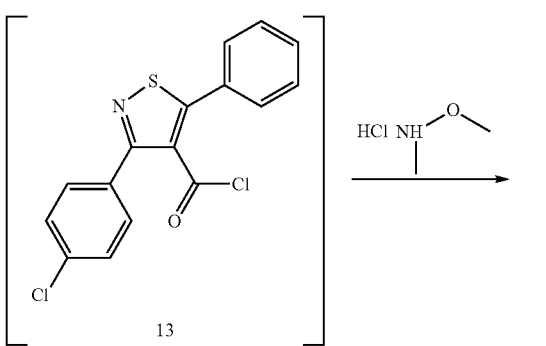

13

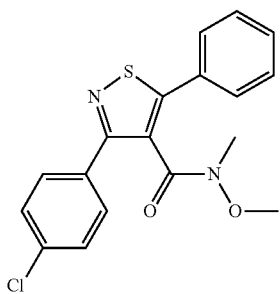

14

To a suspension of 12 (700 mg) in CH$_2$Cl$_2$ (10 ml) is added oxalyl chloride (0.76 ml) followed by one drop of DMF. A vigorous reaction took place. After stirring for several minutes a clear solution is obtained, which is stirred overnight. The reaction mixture is concentrated and stripped with toluene (2×). The yellow solid is dissolved in CH$_2$Cl$_2$ (10 ml), O,N-Dimethyl-hydroxylamine hydrochloride (432 mg) is added followed by the addition of 1.5 ml of Et$_3$N. After stirring for 1 h the mixture is concentrated. The solid residue is partitioned between EtOAc and 1N HCl. After washing, the layers are separated and the organic layer is washed once more with 1 N HCl, sat. NaHCO$_3$, brine, dried and concentrated. The residue is purified by flash column chromatography (20% EtOAc in heptane). 667 mg of 14 is obtained as a white crystalline solid with a melting point of 119-120° C.

Step k: 3-(4-Chloro-phenyl)-5-phenyl-isothiazole-4-carbaldehyde (15)

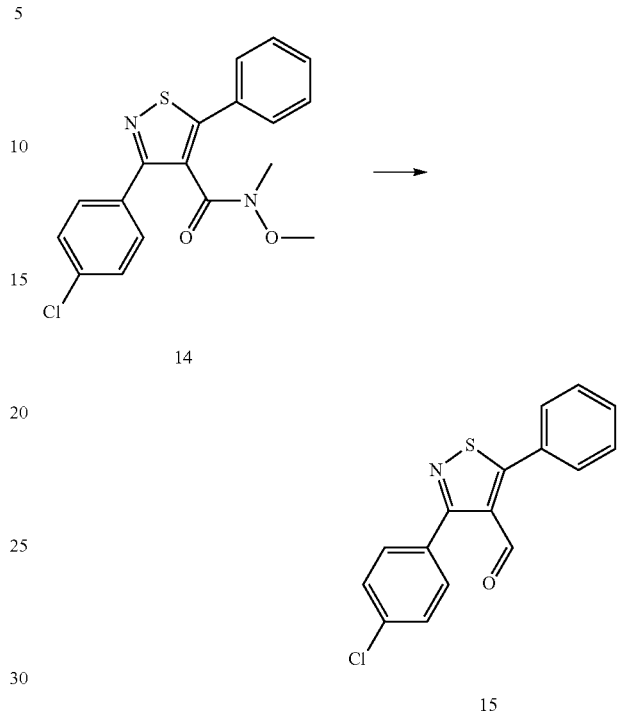

A solution of 14 (359 mg) in 4 ml of THF is cooled to −78° C. under N$_2$ and to this is added 1.5 ml of DIBALH (1M in hexane). After stirring for 30 min at −78° C., only starting material is observed. The iPrOH/CO$_2$ bath is replaced for an ice bath and stirring is continued at 0° C. for 2 h. TLC shows complete conversion. The mixture is re-cooled to −78° C. and the reaction mixture is quenched with 1N HCl (5 ml). The cooling bath is removed and the reaction mixture is diluted with 1N HCl (50 ml) and EtOAc (50 ml). The layers are separated and the organic layer is washed once more with 1N HCl (50 ml). The organic layer is washed with brine, dried and concentrated. 286 mg of 15 are obtained as a white solid with melting point: 148-149° C.

Step l: [3-(4-Chloro-phenyl)-5-phenyl-isothiazol-4-yl]-pyridin-3-yl-methanol (16)

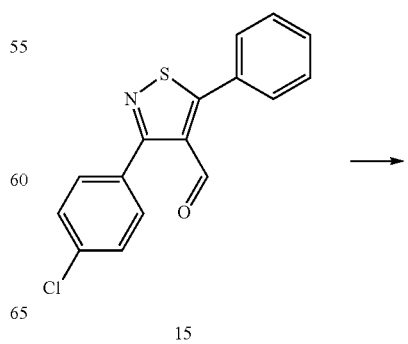

15

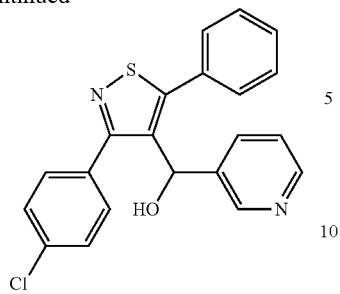

16

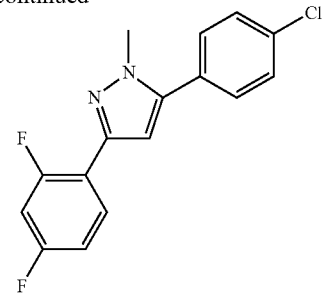

20

A solution of 3-bromopyridine (103 mg) in 2.5 ml of ether is cooled to −78° C. under $N_2$ and to this is added drop-wise a BuLi solution (0.375 ml, 1.6 M in hex). After stirring for 15 min, a solution of 15 (150 mg) in THF is added drop-wise. Stirring is continued for 20 min at −78° C., the red colored reaction mixture is quenched with water (5 ml) and the cooling bath is removed. Water (25 ml) and EtOAc (30 ml) are added. After washing, the layers are separated, the organic layer is washed with brine, dried and concentrated to afford an orange foam (200 mg). The material is purified by flash column chromatography (2% MeOH in $CH_2Cl_2$). Desired compound 16 is obtained as white foam showing the expected mass in LCMS ($M^{+1}$:379 and its isotopes at 380; 381 and 382).

Example 2

Preparation of [3-(4-Chloro-phenyl)-5-(2,4-difluoro-phenyl)-1-methyl-1H-pyrazol-4-yl]-pyridin-3-yl-methanol (compound B87; see Table II)

Step a: Mixture of 3-(4-Chloro-phenyl)-5-(2,4-difluoro-phenyl)-1-methyl-1H-pyrazole (19) and 5-(4-Chloro-phenyl)-3-(2,4-difluoro-phenyl)-1-methyl-1H-pyrazole (20)

4-Chloroacetophenone (4 g) is dissolved in toluene (50 ml) and the solution is cooled to 0° C. under nitrogen. Lithium-bis(trimethylsilyl)amide solution (27.2 ml, 1M in THF) is added quickly via syringe with stirring, and the formed anion is allowed to stir for approximately 10 minutes before the addition of 2,4-difluorobenzoyl chloride (2.28 g) in one portion. The reaction mixture is removed from ice-bath and allowed to stand for 5 minutes. Acetic acid (20 ml) is added followed by EtOH (100 ml) and THF (50 ml) and finally methyl hydrazine (20.4 g). The resulting solution is added to NaOH 1M solution and extracted twice with EtOAc. The combined organic layers are washed with brine, dried and concentrated to afford a crude material that is purified by flash column chromatography (30% EtOAc in cyclohexane). This afforded an inseparable mixture of (19) and (20), in a ratio 1:1, as a pale yellow oil (3.3 g).

Step b: Preparation of 3-(4-Chloro-phenyl)-5-(2,4-difluoro-phenyl)-1-methyl-1H-pyrazole-4-carbaldehyde (23) and 5-(4-Chloro-phenyl)-3-(2,4-difluoro-phenyl)-1-methyl-1H-pyrazole-4-carbaldehyde (24)

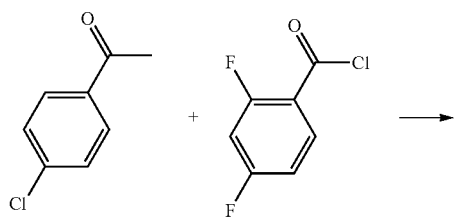

17                18

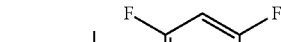

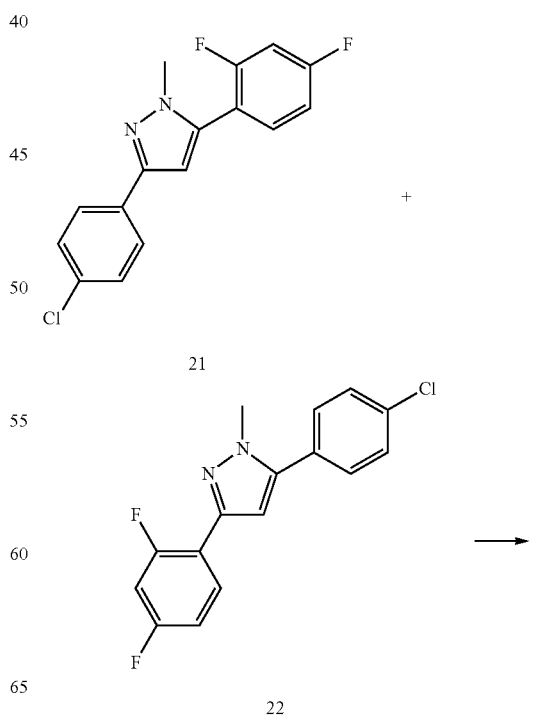

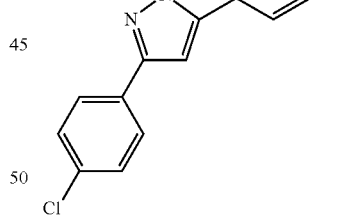

19

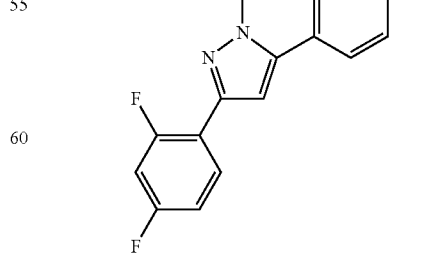

22

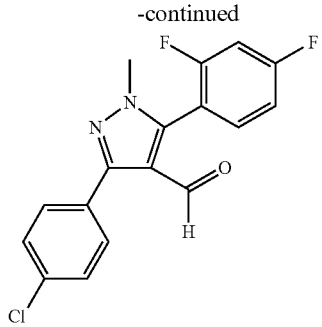

23

The mixture above (2 g) is dissolved in DMF (3.1 ml) and phosphorus pentachloride (2 g) is added. The reaction is stirred overnight at 70° C. The reaction is cooled to room temperature, diluted with water and neutralized with a saturated solution of Na$_2$CO$_3$. The aqueous layer is extracted with DCM (3×50 ml), dried and concentrated in vacuo. The residue is purified by flash column chromatography (20% EtOAc in cyclohexane). The desired compounds, (23) and (24) are isolated as a foam (0.41 g) and as a white crystalline solid (0.43 g) respectively.

Step c: [3-(4-Chloro-phenyl)-5-(2,4-difluoro-phenyl)-1-methyl-1H-pyrazol-4-yl]-pyridin-3-yl-methanol (25) (compound B87 see Table II)

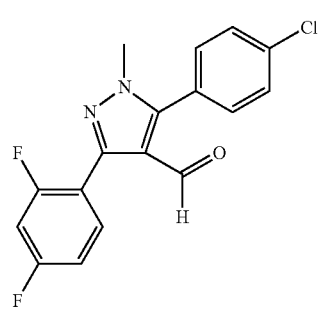

23

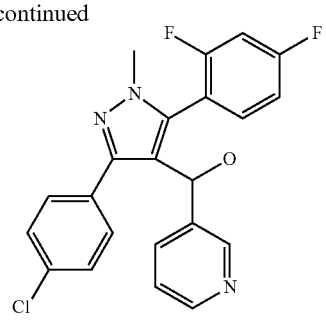

25

A solution of 3-bromopyridine (0.24 g) in 5 ml of THF (5 ml) is cooled to 0° C. under N$_2$ and to this is added drop-wise an isopropylmagnesium chloride lithium chloride complex solution (2.26 ml, 1 M in THF). After stirring for 2.5 hours at room temperature, a solution of 23 (0.41 g) in THF (5 ml) is added drop-wise. The reaction is allowed to reach room temperature and the stirring is continued for 3 hours. The reaction mixture is quenched with water and extracted twice with EtOAc (50 ml). The combined organic layers are washed with brine, dried and concentrated to afford a crude material that is purified by flash column chromatography (30% EtOAc in heptane). The desired compound 25 (0.23 g) is obtained as a white solid with melting point: 117-119° C.

Example 3

Preparation of [5-(4-Chloro-phenyl)-3-(2,4-difluoro-phenyl)-1-methyl-1H-pyrazol-4-yl]-pyridin-3-yl-methanol (26) (compound C84 see Table III)

24

26

The same conditions reported for Step c (Example 2) are applied to 24 (0.43 g). The desired compound is isolated as white solid (0.40 g) with a melting point: 190-194° C.

Although the invention is described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication are specifically and individually indicated to be so incorporated by reference.

BIOLOGICAL EXAMPLES

This example illustrates the fungicidal properties of compounds of formula (Ia-c). The tests are performed as follows:

*Botrytis cinerea* (Gray mould): Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is determined photometrically after 72 hours.

The following compounds give at least 80% control of *Botrytis cinerea* at 20 ppm: A1, A2, A4, A14, A44, A62, A63, A64, A65, A66, A67, A68, A69, A70, A71, A72, A73, A74, A75, A76, A77, A78, A79, A80, B84, B85, B86, C84.

*Erysiphe graminis* f.sp. tritici (Wheat powdery mildew): Barley leaf segments are placed on agar in multiwell plates (24-well format) and sprayed with test solutions. After drying, the leaf disks are inoculated with spores of the fungus. After appropriate incubation the activity of a compound is assessed 7 dpi (days after inoculation) as preventive fungicidal activity.

The following compounds give at least 80% control of *Erysiphe graminis* at 200 ppm: A1, A2, A14, A44, A62, A63, A64, A65, A66, A67, A69, A70, A71, A72, A76, A77, A78, A79, A80, B84, B86, B90, C84, C85, C87.

*Pyrenophora teres* (Net blotch): Barley leaf segments are placed on agar in multiwell plates (24-well format) and sprayed with test solutions. After drying, the leaf disks are inoculated with a spore suspension of the fungus. After appropriate incubation the activity of a compound is assessed 4 dpi (days after inoculation) as preventive fungicidal activity.

The following compounds give at least 80% control of *Pyrenophora teres* at 200 ppm: A1, A2, A14, A62, A63, A65, A66, A67, A68, A69, A70, A71, A72, A75, A76, A77, A78, A79, A80.

*Puccinia recondita* (Brown rust): Wheat leaf segments are placed on agar in multiwell plates (24-well format) and sprayed with test solutions. After drying, the leaf disks are inoculated with a spore suspension of the fungus. After appropriate incubation the activity of a compound is assessed 8 dpi (days after inoculation) as preventive fungicidal activity.
The following compounds give at least 80% control of *Puccinia recondita* at 200 ppm:
A1, A2, A14, A16, A62, A63, A66, A67, A68, A69, A70, A71, A72, A75, A76, A77, A78, A79, A80, B85, B86, B87, B90, C84, C85, C87.

*Septoria tritici* (Leaf Blotch): Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is determined photometrically after 72 hours. The following compounds give at least 80% control of *Septoria tritici* at 20 ppm: A1, A2, A4, A14, A16, A44, A62, A63, A64, A65, A66, A67, A68, A69, A70, A71, A72, A73, A74, A75, A76, A77, A78, A79, A80, B84, B85, B86, B87, B90, B91, C84, C85, C87.

The invention claimed is:
1. A compound of formula I:

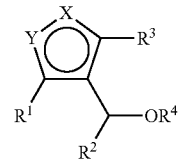

wherein:
X is S, N or $NR^5$ and Y is N or $NR^5$, with the proviso that one, but not both, of X or Y is N;
$R^1$ and $R^3$ are, independently, hydrogen, or optionally substituted alkyl, alkenyl, alkynyl, heterocyclyl, trialkylsilyl, arylalkyl, aryloxyalkyl, aryl or heteroaryl, with the proviso that they are not both hydrogen;
$R^2$ is optionally substituted 5- or 6-membered heteroaryl;
$R^4$ is hydrogen or acyl;
$R^5$ is hydrogen or optionally substituted alkyl, alkenyl, alkynyl, heterocyclyl, trialkylsilyl, arylalkyl, aryloxyalkyl, arylthioalkyl, aryl or heteroaryl;
or a salt or N-oxide thereof.

2. The compound of claim 1, wherein X is S and Y is N.
3. The compound of claim 1, wherein X is $NR^5$ and Y is N.
4. The compound of claim 1, wherein X is N and Y is $NR^5$.
5. The compound of claim 1, wherein $R^1$ and $R^3$ are, independently, hydrogen or optionally substituted alkyl, aryloxyalkyl, aryl or heteroaryl.
6. The compound of claim 1, wherein $R^1$ and $R^3$ are, independently, hydrogen or optionally substituted alkyl, phenyl or 5- or 6-membered heteroaryl.
7. The compound of claim 1, wherein $R^4$ is hydrogen.
8. The compound of claim 1, wherein $R^5$ is hydrogen or optionally substituted alkyl, alkenyl or alkynyl.
9. The compound of claim 1, wherein $R^5$ is hydrogen or optionally substituted trialkylsilyl or arylalkyl.
10. The compound of claim 1, wherein at least one of $R^1$, $R^3$ and $R^5$ is not hydrogen.
11. The compound of claim 1, wherein
X is S and Y is N;
$R^1$ and $R^3$ are, independently, optionally substituted aryl or heteroaryl;
$R^2$ is optionally substituted 5 or 6-membered heteroaryl; and
$R^4$ is hydrogen or acyl.
12. The compound of claim 11, wherein
X is S and Y is N;
$R^1$ is 3-chloro-phenyl, 4-chloro-phenyl, 2-fluoro-phenyl, 2,4-difluoro-phenyl or 2-thienyl;
$R^2$ is 3-pyridyl or 3-pyrimidinyl;
$R^3$ is phenyl, 4-chloro-phenyl, 2,4-dichloro-phenyl, 4-bromo-phenyl or 2-fluoro-4-chloro-phenyl; and
$R^4$ is hydrogen.
13. The compound of claim 1, wherein
X is $NR^5$ and Y is N;
$R^1$ and $R^3$ are, independently, optionally substituted aryl or heteroaryl;
$R^2$ is optionally substituted 5 or 6-membered heteroaryl;

$R^4$ is hydrogen or acyl; and $R^5$ is hydrogen or optionally substituted alkyl, arylalkyl, aryloxyalkyl or aryl.

14. The compound of claim 13, wherein

X is $NR^5$ and Y is N;

$R^1$ is 4-chloro-phenyl, 4-bromo-phenyl, 2-fluoro-phenyl, 3-fluoro-phenyl, 4-fluoro-phenyl or 2,4-difluoro-phenyl;

$R^2$ is 3-pyridyl;

$R^3$ is 4-methoxy-phenyl, 4-chloro-phenyl or 2,4-difluoro-phenyl;

$R^4$ is hydrogen; and $R^5$ is methyl or benzyl.

15. The compound of claim 1, wherein

X is N and Y is $NR^5$;

$R^1$ and $R^3$ are, independently, optionally substituted aryl or heteroaryl;

$R^2$ is optionally substituted 5 or 6-membered heteroaryl;

$R^4$ is hydrogen or acyl; and $R^5$ is hydrogen, optionally substituted alkyl or aryl.

16. The compound of claim 15, wherein

X is N and Y is $NR^5$;

$R^1$ is 4-chloro-phenyl, 2-fluoro-phenyl, 3-fluoro-phenyl or 2,4-difluoro-phenyl;

$R^2$ is 3-pyridyl;

$R^3$ is 4-chloro-phenyl or 4-fluoro-phenyl;

$R^4$ is hydrogen; and $R^5$ is methyl.

17. A composition for treating fungal infection comprising a compound of formula I as defined in claim 1, and an agriculturally acceptable carrier or diluent.

18. The composition of claim 17, further comprising at least one additional fungicide.

19. A method of treating fungal infection in plants and/or plant propagation material comprising applying to the plant or plant propagation material or the locus thereof a fungicidally effective amount of a compound of formula I as defined in claim 1.

20. A composition comprising a compound of formula I as defined in claim 1, and a pharmaceutically acceptable carrier or diluent.

* * * * *